(12) United States Patent
Mitragotri et al.

(10) Patent No.: US 11,191,774 B2
(45) Date of Patent: Dec. 7, 2021

(54) DRUG FORMULATIONS FOR CANCER TREATMENT

(71) Applicant: The Regents of the University of California, Oakland, CA (US)

(72) Inventors: Samir Mitragotri, Lexington, MA (US); Marta Broto, Barcelona (ES); Kathryn M. Camacho, Los Angeles, CA (US); Stefano Menegatti, Raleigh, NC (US)

(73) Assignee: The Regents of the University of California, Oakland, CA (US)

( * ) Notice: Subject to any disclaimer, the term of this patent is extended or adjusted under 35 U.S.C. 154(b) by 478 days.

(21) Appl. No.: 15/779,232

(22) PCT Filed: Nov. 23, 2016

(86) PCT No.: PCT/US2016/063668
§ 371 (c)(1),
(2) Date: May 28, 2018

(87) PCT Pub. No.: WO2017/091767
PCT Pub. Date: Jun. 1, 2017

(65) Prior Publication Data
US 2020/0306284 A1 Oct. 1, 2020

Related U.S. Application Data

(60) Provisional application No. 62/394,567, filed on Sep. 14, 2016, provisional application No. 62/259,757, filed on Nov. 25, 2015.

(51) Int. Cl.
*A61K 31/7072* (2006.01)
*A61P 35/00* (2006.01)
(Continued)

(52) U.S. Cl.
CPC ........ *A61K 31/7072* (2013.01); *A61K 9/1273* (2013.01); *A61K 31/506* (2013.01); *A61K 31/513* (2013.01); *A61P 35/00* (2018.01)

(58) Field of Classification Search
None
See application file for complete search history.

(56) References Cited

U.S. PATENT DOCUMENTS 7,597,950 B1 10/2009 Stallacci
2005/0142178 A1* 6/2005 Daftary ................ A61K 31/704
424/450

(Continued)

FOREIGN PATENT DOCUMENTS

EP 0400610 12/1990
WO 2010129547 A1 11/2010

(Continued)

OTHER PUBLICATIONS

Ashish V. Kalra and Robert B. Campbell. "Development of 5-FU and Doxorubicin-Loaded Cationic Liposomes against Human Pancreatic Cancer: Implications for Tumor Vascular Targeting." Pharmaceutical Research, vol. 23, No. 12, Dec. 2006, pp. 2809-2817. (Year: 2006).*

(Continued)

*Primary Examiner* — Isaac Shomer
(74) *Attorney, Agent, or Firm* — Nixon Peabody LLP; David S. Resnick; Nicole D. Kling

(57) ABSTRACT

Compounds and pharmaceutical formulations containing these compounds are described. Also described are methods of making and using the compounds. The compounds include nucleobases, nucleobase analogues, or combinations thereof. In one embodiment, a nucleobase analogue is combined with doxorubicin and encapsulated within a liposome for use in inhibiting or preventing the growth of cancer cells. Further described are pharmaceutical compositions contain- (Continued)

ing two or more therapeutically active agents encapsulated within a vesicle, such as a liposome, wherein the molar ratio of the agents provides a synergistic therapeutic effect.

14 Claims, 10 Drawing Sheets

(51) Int. Cl.
   *A61K 9/127* (2006.01)
   *A61K 31/506* (2006.01)
   *A61K 31/513* (2006.01)

(56) References Cited

U.S. PATENT DOCUMENTS

| | | | |
|---|---|---|---|
| 2008/0107722 A1* | 5/2008 | Tardi | A61K 9/1278 424/450 |
| 2010/0247620 A1* | 9/2010 | Castor | A61K 31/4745 424/450 |
| 2011/0250284 A1 | 10/2011 | Lavik et al. | |
| 2012/0197060 A1 | 6/2012 | Ray et al. | |
| 2013/0022665 A1* | 1/2013 | Niitsu | A61K 9/10 424/450 |
| 2014/0178462 A1* | 6/2014 | Panzner | A61K 9/1272 424/450 |
| 2018/0036419 A1 | 2/2018 | Camacho et al. | |

FOREIGN PATENT DOCUMENTS

| | | |
|---|---|---|
| WO | 2011/112482 | 9/2011 |
| WO | 2011112482 | 9/2011 |
| WO | 2012142362 A2 | 10/2012 |
| WO | 2014/194848 | 12/2014 |
| WO | 2014194848 | 12/2014 |
| WO | 2016/145096 | 9/2016 |
| WO | 2016145096 | 9/2016 |

OTHER PUBLICATIONS

Amir Maghsoudi, Seyed Abbas Shojaosadati, and Ebrahim Vasheghani Farahani. "5-Fluorouracil-Loaded BSA Nanoparticles: Formulation Optimization and In Vitro Release Study." AAPS PharmSciTech, vol. 9, No. 4, Dec. 2008, pp. 1092-1096. (Year: 2008).*
Laurence Gallois, Marina Fiallo, Arlette Garnier-Suillerot. "Comparison of the interaction of doxorubicin, daunorubicin, idarubicin and idarubicinol with large unilamellar vesicles Circular dichroism study." Biochimica et Biophysica Acta vol. 1370, 1998, pp. 31-40. (Year: 1998).*
Vandana Soni, DV Kohli, & S. K. Jain. "Transferrin-conjugated liposomal system for improved delivery of 5-fluorouracil to brain." Journal of Drug Targeting, Jan. 2008; 16(1): pp. 73-78. (Year: 2008).*
José L. Arias. "Novel Strategies to Improve the Anticancer Action of 5-Fluorouracil by Using Drug Delivery Systems." Molecules 2008, 13, pp. 2340-2369; DOI: 10.3390/molecules13102340. (Year: 2008).*
Ofonime Udofot, Kevin Affram, Bridg'ette Israel and Edward Agyare. "Cytotoxicity of 5-fluorouracil-loaded pH-sensitive liposomal nanoparticles in colorectal cancer cell lines." Integrative Cancer Science and Therapeutics, vol. 2(5), 2015, pp. 245-252, published Oct. 9, 2015. (Year: 2015).*
Kathryn M. Camacho et al. "DAFODIL: A novel liposome-encapsulated synergistic combination of doxorubicin and 5FU for low dose chemotherapy." Journal of Controlled Release 229 (2016) 154-162. (Year: 2016).*
Kathryn Militar Camacho. "Discovery and Delivery of Synergistic Chemotherapy Drug Combinations to Tumors." PhD Thesis, University of California Santa Barbara, Dec. 2015, pp. i-xvi and 1-168 (184 total sheets). (Year: 2015).*

Andreia, et al., "Encapsulation of 5-fluorouracil in liposomes for topical administration", *ACTA Scientiarum, Technology*, 53-61 (2003).
Andresen, et al., "Advanced strategies in liposomal cancer therapy: problems and prospects of active and tumor specific drug release", *Prog Lipid Res*, 44(1):68-97 (2005).
Bandyopadhyay, et al., "Doxorubicin in combination with a small TGFbeta inhibitor: a potential novel therapy for metastatic breast cancer in mouse models", *PLOS ONE*, 5(4):e10365 (2010).
Barenholz, "Liposome application: problems and prospects", *Curr Opinion Colloid & Interface Sci.*, 6(1):66-77 (2001).
Barenholz, et al., "Stability of liposomal doxorubicin formulations: problems and prospects", *Med Res Rev.* 13(4):449-491 (1993).
Barenholz, "Doxil®—the first FDA-approved nano-drug: lessons learned" *J Cont Release*, 160(2):117-34 (2012).
Bennett, et al., "Cationic lipids enhance cellular uptake and activity of phosphorothioate antisense oligonucleotides", *Mol. Pharm*, 41(6):1023-33 (1992).
Buzzoni, et al., "Adjuvant chemotherapy with doxorubicin plus cyclophosphamide, methotrexate, and fluorouracil in the treatment of resectable breast cancer with more than three positive axillary nodes", *J Clin Oncol*, 9(12):2134-40 (1991).
Cabanes, et al., "Comparative study of the antitumor activity of free doxorubicin and polyethylene glycol-coated liposomal doxorubicin in a mouse lymphoma model", *Clin. Cancer Res.*, 4:499-505 (1998).
Cai, et al., "Localized doxorubicin chemotherapy with a biopolymeric nanocarrier improves survival and reduces toxicity in xenografts of human breast cancer", *J Control Release*, 146(2):212-8 (2010).
Camacho, et al., "DAFODIL: a novel liposome-encapsulated synergistic combination of doxorubicin and 5FU for low dose chemoterapry", *Journal of Controlled Release*, 229:154-162 (2016).
Campbell, et al., "Cationic charge determines the distribution of liposomes between the vascular and extravascular compartments of tumors", *Cancer Res.*, 62:6831-6 (2002).
Cazap, et al., "Phase II trials of 5-FU, doxorubicin, and cisplatin in advanced, measurable adenocarcinoma of the lung and stomach", *Cancer Treat Rep.*, 70(6):781-3 (1986).
Chang, et al., "Biodistribution, pharmacokinetics and microSPECT/CT imaging of 188Re-bMEDA-liposome in a C26 murine colon carcinoma solid tumor animal model", *Anticancer Res.*, 27(4B):2217-25 (2007).
Charrois and Allen, "Multiple injections of pegylated liposomal Doxorubicin: pharmacokinetics and therapeutic activity", *J. Pharmacology Exp. Ther.*, 306(3):1058-67 (2003).
Chen, et al., "Hyaluronic acid-based drug conjugates: state-of-the-art and perspectives", *J Biomed Nanotechnol*, 10(1):4-16 (2014).
Chou, "Theoretical basis, experimental design, and computerized simulation of synergism and antagonism in drug combination studies", Pharmacol Rev, 58(3):621-81 (2006).
Chou and Talalay, "Quantitative analysis of dose-effect relationships: the combined effects of multiple drugs or enzyme inhibitors", Adv. Enzyme Reg., 22:27-55 (1984).
Cullinan, et al., "A comparison of three chemotherapeutic regimens in the treatment of advanced pancreatic and gastric carcinoma. Fluorouracil vs fluorouracil and doxorubicin vs fluorouracil, doxorubicin, and mitomycin", *JAMA*, 253(14):2061-7 (1985).
Debnath, et al., "Amino and carboxy functionalized modified nucleosides: A potential class of inhibitors for angiogenin", *Bioorganic chemistry*, 52:56-61 (2014).
Diasio and Harris, "Clinical pharmacology of 5-fluorouracil", Clin Pharmacokinetics, 16(4):215-37 (1989).
Du, et al., "Quercetin greatly improved therapeutic index of doxorubicin against 4T1 breast cancer by its opposing effects on HIF-1α in tumor and normal cells". Cancer Chemotherapy Pharmacol., 65(2):277-87 (2010).
Duncan, "Development of Hpma copolymer-anticancer conjugates: clinical experience and lessons learnt", *Adv Drug Deliv Rev*, 61(13):1131-48 (2009).
Duncan, "Polymer conjugates as anticancer nanomedicines", *Nature Reviews: Cancer*, 6:688-701 (2006).
Ellerhorst, et al., "Phase II trial of doxil for patients with metastatic melanoma refractory to frontline therapy", *Oncol Rep*, 6(5):1097-1106 (1999).

(56) References Cited

OTHER PUBLICATIONS

Friend, et al., "Endocytosis and intracellular processing accompanying transfection mediated by cationic liposomes", *Biochim Biophy Acta*, 1278(1):41-50 (1996).
Gabra, et al., "Weekly doxorubicin and continuous infusional 5-fluorouracil for advanced breast cancer", *Br J Cancer*, 74:2008-12 (1996).
Grant, et al., "Single-agent chemotherapy trials in small-cell lung cancer, 1970 to 1990: the case for studies in previously treated patients", *J Clin Oncol.*, 10(3):484-98 (1992).
Greco, et al., "Combination therapy: Opportunities and challenges for polymer-drug conjugates as anticancer nanomedicines", *Adv Drug Delivery Rev.*, 61:1203-13 (2009).
Gordon, et al., "Recurrent epithelial ovarian carcinoma: a randomized phase III study of pegylated liposomal doxorubicin versus topotecan", *J Clin Oncol*, 19(14):3312-22 (2001).
Gubernator, "Active methods of drug loading into liposomes: recent strategies for stable drug entrapment and increased vivo activity", *Expert Opinion on Drug Delivery*, 8(5):565-580 (2011).
Halford, et al., "A phase II study evaluating the tolerability and efficacy of CAELYX (liposomal doxorubicin, Doxil) in the treatment of unresectable pancreatic carcinoma", *Ann Oncol.*, 12(10):1399-1402 (2001).
Hansen, et al., "Continuous 5-fluorouracil infusion in refractory carcinoma of the breast", *Breast Cancer Res Treat.*, 10(2):145-9 (1987).
Haran, et al., "Transmembrane ammonium sulfate gradients in liposomes produce efficient and stable entrapment of amphipathic weak bases", *Biochim Biophy Acta*, 1151(2):201-15 (1993).
Harada, et al., "A phase I/II trial of irinotecan plus amrubicin supported with G-CSF for extended small-cell lung cancer", *Jpn J Clin Oncol.*, 44(2):127-33 (2014).
Hortobagyi, et al., "Evaluation of high-dose versus standard FAC chemotherapy for advanced breast cancer in protected environment units: a prospective randomized study", *J Clin Oncol.*, 5(3):354-64 (1987).
Judson, et al., "Randomised phase Ii trial of pegylated liposomal doxorubicin (Doxil/Caelyx) versus doxorubicin in the treatment of advanced or metastatic soft tissue sarcoma: a study by the EORTC Soft Tissue and Bone Sarcoma Group", *Eur J Cancer*, 37(7):870-7 (2001).
Kaiser, et al., "5-Fluorouracil in vesicular phospholipid gels for anticancer treatment: entrapment and release properties", *Intl J Pharm*, 256(1-2):123-31 (2003).
Kalra and Campbell, "Development of 5-FU and doxorubicin-loaded cationic liposomes against human pancreatic cancer: Implications for tumor vascular targeting", *Pharm Res.*, 23(12):2809-17 (2006).
Klein, et al., "Prospective Randomized Trial Using 5-Fluorouracil, Adriamycin and Methotrexate (FAMTX) versus FAM for Treatment of Advanced Gastric Cancer", *Onkologie*, 15:364-367 (1992).
Klibanov, et al., "Activity of amphipathic poly(ethylene glycol) 5000 to prolong the circulation time of liposomes depends on the liposome size and is unfavorable for immunoliposome binding to target", *Biochimt Biophy Acta*, 1062:142-8 (1991).
Krakoff, "Chemotherapy of gastrointestinal cancer", *Cancer*, 30(6):1600-03 (1972).
Lammers, et al., "Effect of physicochemical modification on the biodistribution and tumor accumulation of HPMA copolymers", *J Control Release*, 110(1):103-18 (2005).
Lancet, et al., "Phase 2 trial of CPX-351, a fixed 5:1 molar ratio of cytarabine/daunorubicin, vs cytarabine/daunorubicin in older adults with untreated AML", *Blood*, 123(21):3239-46 (2014).
Levchenko, et al, "Liposome clearance in mice: the effect of a separate and combined presence of surface charge and polymer coating", *Intl J Pharm*, 240:95-102 (2002).
Levi, et al., "Analysis of a prospectively randomized comparison of doxorubicin versus 5-fluorouracil, doxorubicin, and BCNU in advanced gastric cancer: implications for future studies", *J Clin Oncol*, 4(9):1348-55 (1986).

Liu, et al., "Codelivery of Doxorubicin and Paclitaxel by Cross-Linked Multilamellar Liposome enables synergistic Antitumor activity", *Molecular Pharmaceutics*, 11:1651-61 (2014).
Liu, et al., "Comparison of the therapeutic efficacy of 188Rhenium-liposomes and liposomal doxorubicin in a 4T1 murine orthotopic breast cancer model", *Oncol Rep*, 27(3):678-84 (2012).
Longley and Johnston, "5-Fluorouracil: Apoptosis, Cell Signaling, and Human Diseases" 263-278 (2007).
Longley, et al., 5-fluorouracil: mechanisms of action and clinical strategies. *Nat Rev Cancer*, 3(5):330-8 (2001).
Lyass, et al., "Correlation of toxicity with pharmacokinetics of pegylated liposomal doxorubicin (Doxil) in metastatic breast carcinoma", *Cancer*, 89(5), 1037-47 (2000).
Macdonald, "5-Fluorouracil, doxorubicin, and mitomycin (Fam) combination chemotherapy for advanced gastric cancer", *Annals Internal Med.*, 93:533-6 (1980).
Markovsky, et al., "Anticancer polymer bearing synergistic drug combination is superior to a mixture of individually-conjugated drugs", *J Controlled Release*, 187:145-57 (2014).
Markova, et al., "Tautomeric equilibria of 5-fluorouracil anionic species in water", *J Phys Chem. A*, 114(50):13154-62 (2010).
Mastria, et al., "Doxorubicin-conjugated polypeptide nanoparticles inhibit metastasis in two murine models of carcinoma", J Controlled Release, 208:52-58 (2015).
Mayer, et al., "Influence of vesicle size, lipid composition, and drug-to-lipid ratio on the biological activity of liposomal doxorubicin in mice", *Cancer Res.*, 49:5922-30 (1989).
Mayer, et al., "Ratiometric dosing of anticancer drug combinations: controlling drug ratios after systemic administration regulates therapeutic activity in tumor-bearing mice", *Mol Cancer Ther.*, 5(7):1854-63 (2006).
Moghimi and Szebeni, "Stealth liposomes and long circulating nanoparticles: critical issues in pharmacokinetics, opsonization and protein-binding properties", *Prog Lipid Res.*, 42(6):463-78 (2003).
Muggia, et al., "Phase II study of liposomal doxorubicin in refractory ovarian cancer: antitumor activity and toxicity modification by liposomal encapsulation", *J Clin Oncol*, 15(3):987-93 (1997).
Muggia, et al., "Phase II trial of the pegylated liposomal doxorubicin in previously treated metastatic endometrial cancer: a Gynecologic Oncology Group study", *J Clin Oncol*, 20(9): 2360-4 (2002).
Murad, et al., "Modified therapy with 5-fluorouracil, doxorubicin, and methotrexate in advanced gastric cancer", *Cancer*, 72(1):37-41 (1993).
O'Brien, et al, "Reduced cardiotoxicity and comparable efficacy in a phase III trial of pegylated liposomal doxorubicin HC1 (CAELYX/Doxil) versus conventional doxorubicin for first-line treatment of metastatic breast cancer", *Ann Oncol*, 15(3):440-9 (2004).
Oommen, et al., "Tailored Doxorubicin-Hyaluronan Conjugate as a Potent Anticancer Glyco-Drug: An Alternative to Prodrug Approach", *Macromolecular Bioscience*, 14:327-33 (2014).
Platt, et al., "Anticancer Therapeutics: Targeting Macromolecules and Nanocarriers to Hyaluronan or CD44, a Hyaluronan Receptor", *Molecular Pharmaceutics*, 5(4): 474-486 (2008).
Ryan, et al., "A phase I study of liposomal doxorubicin (Doxil) with topotecan", *Am J Clin Oncol.*, 23(3):297-300 (2000).
Safra, et al., "Pegylated liposomal doxorubicin (doxil): reduced clinical cardiotoxicity in patients reaching or exceeding cumulative doses of 500 mg/m2", *Ann Oncol*, 11(8):1029-33 (2000).
Saito, et al., "Stacking interaction between tryptophan and uracil in a synthetic model compound", *Tetrahedron Letters*, 26(37):4467-4470 (1985).
Song, et al., "Amino acid ester prodrugs of the anticancer agent gemcitabine: synthesis, bioconversion, metabolic bioevasion, and hPEPT1-mediated transport", *Mol Pharm.*, 2(2):157-67 (2005).
Sugimoto, et al., "Elevated expression of DNA topoisomerase II in camptothecin-resistant human tumor cell lines", *Cancer Res*, 50(24) 7962-5 (1990).
Sun, et al., "Bioreducible PAA-g-PEG graft micelles with high doxorubicin loading for targeted antitumor effect against mouse breast carcinoma", *Biomaterials*, 34(28):6818-28 (2013).
Szoka and Papahadjopoulos, "Comparative properties and methods of preparation of lipid vesicles (liposomes)", *Ann Rev Biophy Bioeng*, 9(1): 467-508 (1980).

(56) References Cited

OTHER PUBLICATIONS

Tardi, et al., "Coencapsulation of irinotecan and floxuridine into low cholesteral-containing liposomes that coordinate drug release in vivo", *Biochimica Et Biophysica ACTA-Biomembranes*, 1768(3):678-687 (2007).
Tardi, et al., "In vivo maintenance of synergistic cytarabine:daunorubicin ratios greatly enhances therapeutic efficacy", *Leukemia Research*, 33(1):129-139 (2009).
Thurston, et al., "Cationic liposomes target angiogenic endothelial cells in tumors and chronic inflammation in mice", *J Clin. Invest.*, 101(7):1401-13 (1998).
Vasey, et al., "Phase I clinical and pharmacokinetic study of PK1 [N-(2-hydroxypropyl) methacrylamide copolymer doxorubicin]: first member of a new class of chemotherapeutic agents-drug-polymer conjugates. Cancer Research Campaign Phase I/II Committee", *Clin. Cancer Res*, 5(1):83-94 (1999).
Vanhoefer, et al., "Final results of a randomized phase III trial of sequential high-dose methotrexate, fluorouracil, and doxorubicin versus etoposide, leucovorin, and fluorouracil versus infusional fluorouracil and cisplatin in advanced gastric cancer: A trial of the European Organization for Research and Treatment of Cancer Gastrointestinal Tract Cancer Cooperative Group.", *J Clin Oncol*, 18(14):2648-57 (2000).
Walton, et al., "Constitutive expression of human Bcl-2 modulates nitrogen mustard and camptothecin induced apoptosis", *Cancer Res*, 53(8):1853-61 (1993).
Wang, et al., "Star-shape copolymer of lysine-linked di-tocopherol polyethylene glycol 2000 succinate for doxorubicin delivery with reversal of multidrug resistance", *Biomaterials*, 33(28):6877-88 (2012).
Wang, et al., "Dexamethasone as a chemosensitizer for breast cancer chemotherapy: potentiation of the antitumor activity of adriamycin, modulation of cytokine expression, and pharmacokinetics", *Int J Oncol.*, 30(4):947-53 (2007).
Wang, et al., "Doxorubicin induces apoptosis in normal and tumor cells via distinctly different mechanisms. Intermediacy of H(2)O(2)- and p53-dependent pathways", *J Biol Chem*, 279(24):25535-43 (2004).
Webb, et al., "Randomized trial comparing epirubicin, cisplatin, and fluorouracil versus fluorouracil, doxorubicin, and methotrexate in advanced esophagogastric cancer", *J Clin Oncol*, 15(1):261-7 (1997).
Wils, et al., "Sequential high-dose methotrexate and fluorouracil combined with doxorubicin—a step ahead in the treatment of advanced gastric cancer: a trial of the European Organization for Research and Treatment of Cancer Gastrointestinal Tract Cooperative Group", *J Clin Oncol*, 9(5):827-31 (1991).
Xenidis, et al., "A multicenter phase II study of pegylated liposomal doxorubicin in combination with irinotecan as second-line treatment of patients with refractory small-cell lung cancer", *Cancer Chemother Pharmacol*, 68(1):63-8 (2011).
Zelphati and Szoka, "Mechanism of oligonucleotide release from cationic liposomes", *PNAS*, 93(21):11493-8 (1996).
International Search Report for PCT/US2016/021587 dated Jun. 16, 2016.
International Search Report for corresponding PCT application PCT/US2016/063668 dated Jun. 12, 2017.
Gordon, et al., "Recurrent epithelial ovarian carcinoma: a randomized phase III study of pegylated liposomal doxorubicin versus topotecan", *J Clin Oncol*, 19(14):3312-22 (2001) (2001).
International Search Report for corresponding PCT application PCT/US2016/021587 dated Jun. 16, 2016.
Klein, et al., "Prospective Randomized Trial Using 5-Fluorouracil, Adriamycin and Methotrexate (FAMTX) versus FAM for Treatment of Advanced Gastric Cancer", Oncology Res Treat., 15:364-367 (1992).
Markova, et al., Tautomeric equilibria of 5-fluorouracil anionic species in water. J Phys Chem., A 2010, 114(50):13154-62 (2010).
O'Brien, et al., "Reduced cardiotoxicity and comparable efficacy in a phase III trial of pegylated liposomal doxorubicin HCI (CAELYX/Doxil) versus conventional doxorubicin for first-line treatment of metastatic breast cancer", Ann Oncol, 15(3):440-9 (2004).
Song, et al., "Amino acid ester prodrugs of the anticancer agent gemcitabine: synthesis, bioconversion, metabolic bioevasion, and hPEPTI-mediated transport", Mol Pharm., 2(2):157-67 (2005).
Tardi, et al., "In vivo maintenance of synergistic cytarabine:daunorubicin ratios greatly enhances therapeutic efficacy", Leukemia Research, 33:1, 129-139 (Jan. 1, 2009).
Wang, et al., "Doxorubicin induces apoptosis in normal and tumor cells via distinctly different mechanisms, intermediacy of H(2)O(2)- and p53-dependent pathways", J Biol Chern, 279(24):25535-43 (2004).
Anselmo et al., "Platelet-like nanoparticles: mimicking shape, flexibility, and surface biology of platelets to target vascular injuries." ACS Nano 8(11):11243-11253 (2014).
Arpicco et al. "Hyaluronic acid conjugates as vectors for the active targeting of drugs, genes and nanocomposites in cancer treatment." Molecules 19(3): 3193-3230 (2014).
Asselin et al., "Monomeric (glycine-proline-hydroxyproline) 10 repeat sequence is a partial agonist of the platelet collagen receptor glycoprotein VI," Biochemical Journal 339(Pt 2):413-418 (1999).
Camacho et al. "Synergistic antitumor activity of camptothecin-doxorubicin combinations and their conjugates with hyaluronic acid." Journal of Controlled Release 210: 198-207 (2015).
Cheung et al. "AIDS-related Kaposi's sarcoma: a phase II study of liposomal doxorubicin." Clinical Cancer Research 5(11): 3432-3437 (1999).
Coller et al., "Thromboerythrocytes. In vitro studies of a potential autologous, semi-artificial alternative to platelet transfusions." The Journal of Clinical Investigation 89(2):546-555 (1992).
Doshi et al., "Platelet mimetic particles for targeting thrombi in flowing blood." Advanced Materials 24(28):3864-3869 (2012).
Du et al. "Quercetin greatly improved therapeutic index of doxorubicin against 4T1 breast cancer by its opposing effects on HIF-1α in tumor and normal cells." Cancer Chemotherapy and Pharmacology 65(2): 277-287 (2010).
Duggan et al. "Pegylated liposomal doxorubicin." Drugs 71(18): 2531-2558 (2011).
Gabizon. "Pegylated liposomal doxorubicin: metamorphosis of an old drug into a new form of chemotherapy." Cancer Investigation 19(4): 424-436 (2001).
Giuliani et al. "New doxorubicin analogs active against doxorubicin-resistant coion tumor xenografts In the nude mouse." Cancer Research 40(12): 4682-4687 (1980).
Goebel et al. "Efficacy and safety of Stealth liposomal doxorubicin in AIDS-related Kaposi's sarcoma." British Journal of Cancer 73(8): 989-994 (1996).
Gubala et al., "Kinetics of immunoassays with particles as labels: effect of antibody coupling using dendrimers as linkers." Analyst 136(12):2533-2541 (2011).
Gubala et al., "Kinetics of immunoassays with particles as labels: effect of antibody coupling using dendrimers as linkers." Analyst 136(12):2533-2541 (2011) [Electronic Supplemental Information, 3 pages].
Harrington et al. "Biodistribution and pharmacokinetics of 111 in-DTPA-labelled pegylated liposomes in a human tumour xenograft model: implications for novel targeting strategies," British Journal of Cancer 83(2): 232-238 (2000).
Ishitsuka et al. "Role of uridine phosphorylase for antitumor activity of 5'-deoxy-5-fluorouridine." GANN Japanese Journal of Cancer Research 71(1): 112-123 (1980).
Lashof-Sullivan et al., "Intravenous hemostats: challenges in translation to patients." Nanoscale 5(22):10719-10728 (2013).
Liu et al. "Perspectives on biologically active camptothecin derivatives." Medicinal Research Reviews 35(4): 753-789 (2015).
Lyseng-Williamson et al. "Pegylated liposomal doxorubicin: a guide to its use in various malignancies." BioDrugs 27(5): 533-540 (2013).
Moysan et al. "Gemcitabine versus modified gemcitabine: a review of several promising chemical modifications." Molecular Pharmaceutics 10(2): 430-444 (2013).

(56) References Cited

OTHER PUBLICATIONS

Pivkin et al., "Effect of red blood cells on platelet aggregation." IEEE Engineering in Medicine and Biology Magazine 28(2):32-37 (2009).

Udhrain et al. "Pegylated liposomal doxorubicin in the treatment of AIDS-related Kaposi's sarcoma." International Journal of Nanomedicine 2(3): 345-352 (2007).

Weiss. "The Hill equation revisited: uses and misuses." The FASEB Journal 11(11): 835-841 (1997).

Focan et al. "Sequential administration of epirubicin and paclitaxel for advanced breast cancer. A phase I randomised trial." Anticancer Research 25(2B): 1211-1217 (2005).

Jacquin et al. "Phase II trial of pegylated liposomal doxorubicin in combination with gemcitabine in metastatic breast cancer patients." American Journal of Clinical Oncology 35(1): 18-21 (2012).

Julka et al. "A phase 2 study of sequential neoadjuvant chemotherapy with gemcitabine and doxorubicin followed by gemcitabine and cisplatin in patients with large or locally advanced operable breast cancer: results from long-term follow-up." Breast Cancer 20(4): 357-362 (2013).

Le et al. "Gemcitabine directly inhibits myeloid derived suppressor cells in BALB/c mice bearing 4T1 mammary carcinoma and augments expansion of T cells from tumor-bearing mice." International Immunopharmacology 9(7-8):900-909 (2009).

Vincent et al. "5-Fluorouracil selectively kills tumor-associated myeloid-derived suppressor cells resulting in enhanced T cell-dependent antitumor immunity." Cancer Research 70(8): 3052-3061 (2010).

Zheng et al. "Role of taxane and anthracycline combination regimens in the management of advanced breast cancer: a meta-analysis of randomized trials." Medicine 94(17): 1-10 (2015).

Zhong et al. "A novel liposomal vaccine improves humoral immunity and prevents tumor pulmonary metastasis in mice." International Journal of Pharmaceutics 399(1-2): 156-162 (2010).

\* cited by examiner

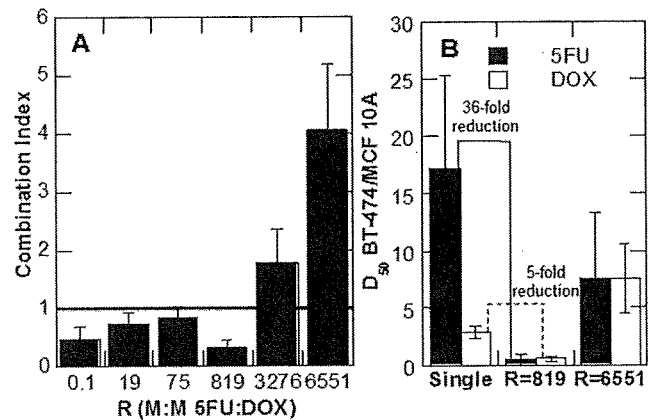
FIG. 2A  FIG. 2B
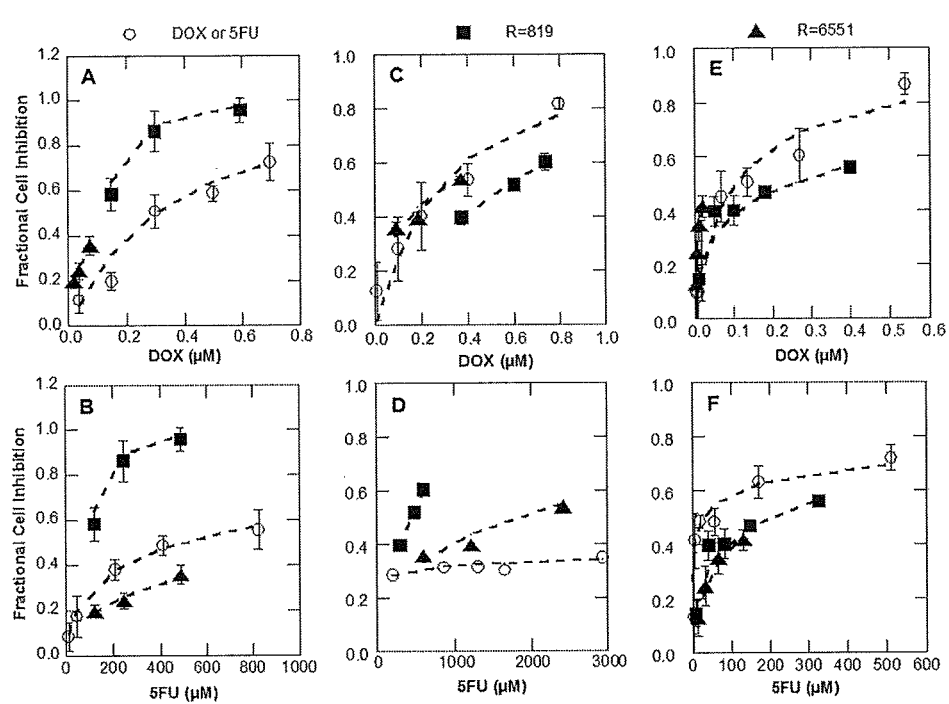
Figures 3A-3F

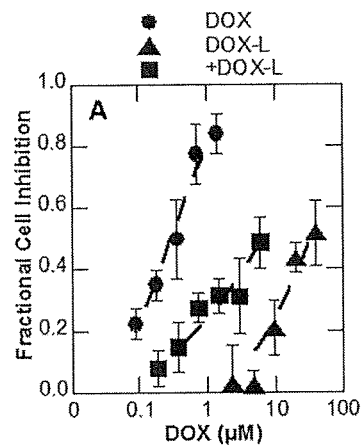
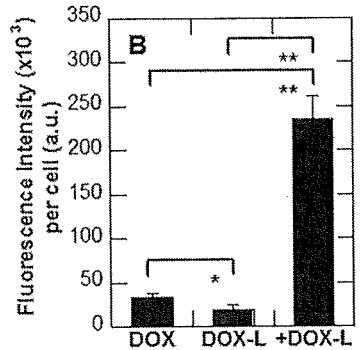
FIG. 4A    FIG. 4B
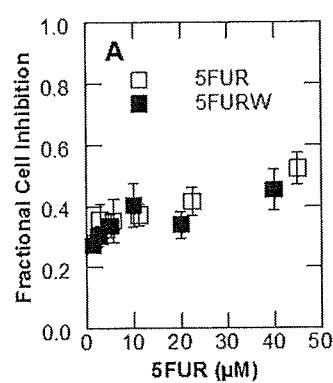
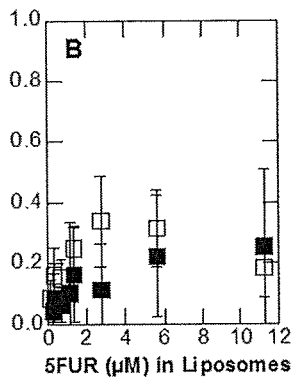
FIG. 5A    FIG. 5B
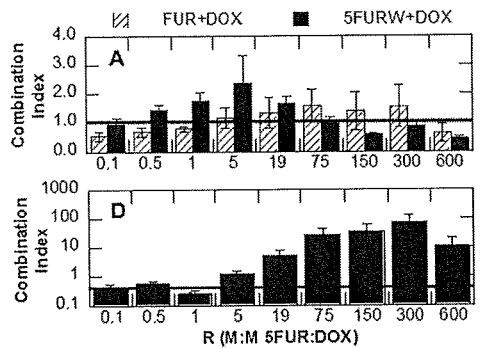
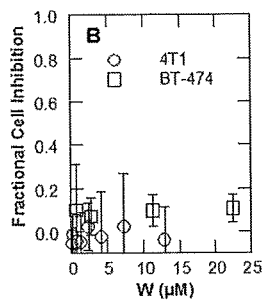
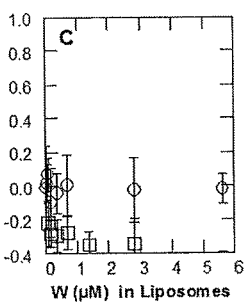
Figures 6A, 6B, 6C and 6D

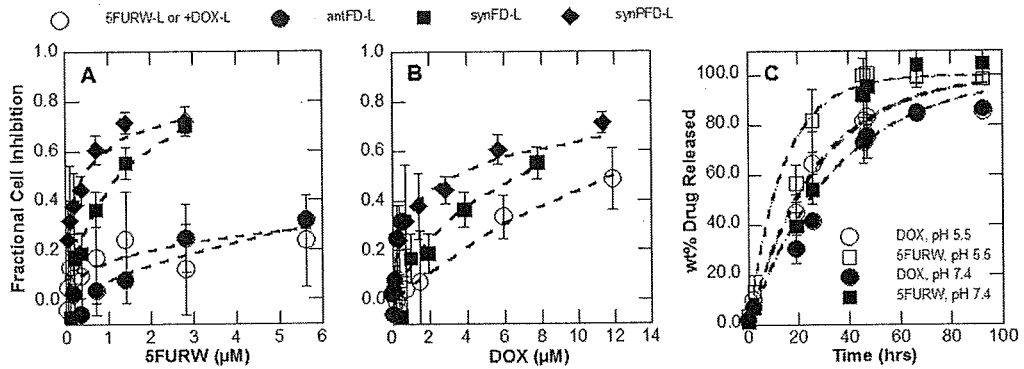
FIG. 7A  FIG. 7B  FIG. 7C
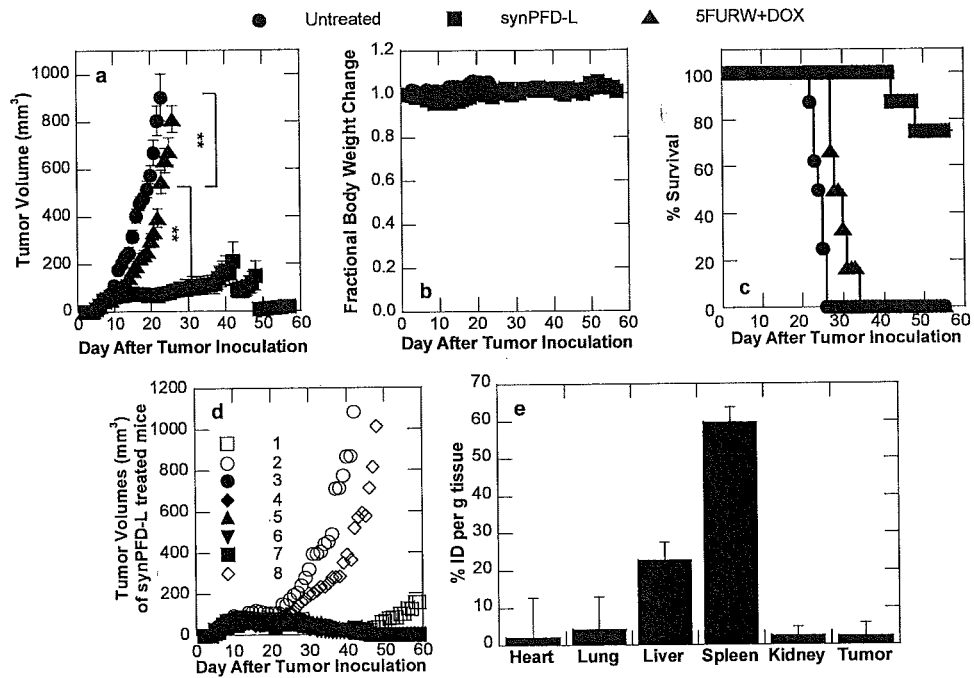
Figures 8A-8E

DRUG FORMULATIONS FOR CANCER TREATMENT

CROSS REFERENCE TO RELATED APPLICATIONS

This application is a National Phase application under 35 U.S.C. § 371 of PCT/US2016/063668, which claims benefit of and priority to U.S. Provisional application No. 62/394,567, filed Sep. 14, 2016 and U.S. Provisional application No. 62/259,757, filed Nov. 25, 2015, the contents of which are hereby incorporated by reference in their entirety.

STATEMENT REGARDING FEDERALLY SPONSORED RESEARCH OR DEVELOPMENT

This invention was made with government support under Grant No. 1 S10 OD010610-01A1 awarded by the National Institutes of Health and Grant No. DMR 1121053 awarded by the National Science Foundation. The government has certain rights in the invention.

FIELD OF THE INVENTION

The invention generally relates to compounds, pharmaceutical compositions and methods of treating cancer in a patient.

BACKGROUND OF THE INVENTION

Over twenty years ago the FDA approved doxorubicin-entrapped liposomes (Doxil), a blockbuster nanoparticle formulation, which has consistently reduced adverse cardiac side effects of the original free drug administration (Lyass, et al., Cancer 2000, 89(5), 1037-47; Safra, et al., Annals of Oncology 2000, 11(8), 1029-1033; Muggia, et al., Journal of Clinical Oncology 1997, 15(3), 987-993). However, this first generation of liposomes has been confronted with challenges, which ultimately question its advantages over free doxorubicin (DOX) (Barenholz, Journal of Controlled Release 2012, 160(2), 117-34; Barenholz, Current Opinion in Colloid & Interface Science 2001, 6(1), 66-77; Moghimi and Szebeni, Progress in Lipid Research 2003, 42(6), 463-478; Andresen, et al., Progress in Lipid Research 2005, 44(1), 68-97). Some clinical trials reported little or only comparable therapeutic efficacy (Judson, et al., European Journal of Cancer 2001, 37(7), 870-877; O'Brien, et al., Annals of Oncology 2004, 15(3), 440-449; Ellerhorst, et al., Oncology Reports 1999, 6(5), 1097-1106; Halford, et al., Annals of Oncology 2001, 12(10), 1399-1402; Muggia, et al., Journal of clinical oncology 2002, 20(9), 2360-2364); whereas other studies showed that liposomal DOX merely increased the tolerable dose, making it difficult to decipher whether liposomal entrapment actually enhances antitumor efficacy (Mayer, et al., Cancer Research 1989, 49, 5922-5930; Cabanes, et al., Clinical Cancer Research 1998, 4, 499-505).

5-fluorouracil (5FU) and DOX are frequently included in combination chemotherapy regimens against gastric cancer (Wils, et al., Journal of Clinical Oncology 1991, 9(5), 827-831; Murad, et al., Cancer 1993, 72(1), 37-41; Macdonald, Annals of Internal Medicine 1980, 93, 533-536; Levi, et al., Journal of Clinical Oncology 1986, 4(9), 1348-1355; Cazap, et al., Cancer treatment reports 1986, 70(6), 781-783; Klein, et al., Oncology Research and Treatment 1992, 15, 364-367; Vanhoefer and Rougier, Journal of Clinical Oncology 2000, 18(14), 2648-2657; Webb and Cunningham, Journal of Clinical Oncology 1997, 15(1), 261-267; Cullinan, et al., JAMA 1985, 253(14), 2061-2067), and have been employed in many clinical trials against breast carcinoma, as well (Hortobagyi and Bodey, Journal of Clinical Oncology 1987, 5(3), 354-364; Buzzoni, et al., Journal of Clinical Oncology 1991, 9(12), 2134-40; Gabra, et al., British Journal of Cancer 1996, 74, 2008-2012). When included in combination chemotherapy regimens, response rates can improve from 15-38% (O'Brien, et al, Annals of Oncology 2004, 15(3), 440-449; Krakoff, Cancer 1972, 30(6), 1600-1603; Hansen, et al., Breast Cancer Research and Treatment 1987, 10(2), 145-149; Gordon, et al., Journal of Clinical Oncology 2001, 19(14), 3312-3322) to 40-50% against advanced gastric cancers (Wils and Klein, Journal of Clinical Oncology 1991, 9(5), 827-831; Murad, et al., Cancer 1993, 72(1), 37-41; Macdonald, Annals of Internal Medicine 1980, 93, 533-536; Klein, et al., Oncology Research and Treatment 1992, 15, 364-367) and 50-75% against advanced breast carcinoma (Hortobagyi and Bodey, Journal of Clinical Oncology 1987, 5(3), 354-364; Buzzoni, et al., Journal of clinical Oncology 1991, 9(12), 2134-40; Gabra, et al., British Journal of Cancer 1996, 74, 2008-2012). However, the median survival time for patients treated with these regimens is still quite low, ranging between 7-9 months. Despite encouraging improvements in therapeutic efficacy, there still remains a clear unmet need to advance these combinations to create more successful therapeutics with more complete responses and longer survival times (Murad, et al., Cancer 1993, 72(1), 37-41; Hortobagyi and Bodey, Journal of Clinical Oncology 1987, 5(3), 354-364).

There is a need for improved formulations containing a combination of chemotherapeutics, particularly for the combination of 5FU and DOX.

Therefore, it is an object of the invention to provide chemical compounds with a beneficial effect against cancer cells.

It is a further object of the invention to provide improved pharmaceutical compositions for delivering two or more therapeutic agents to a patient in need of treatment, and particularly, for reducing or preventing tumor growth in a cancer patient while limiting toxicity from the active agent.

It is yet another object of the invention to provide improved methods of treating cancer in a patient, and more particularly to reduce or prevent tumor growth in a cancer patient with reduced side effects from the same drugs typically delivered alone.

It is another object of the invention to provide improved pharmaceutical compositions for delivering to a patient two or more therapeutically active agents in the same formulation.

It is another object of the invention to provide a method of making chemical compounds with a beneficial anticancer effect.

It is yet another object of the invention to provide methods for making compositions containing these compounds.

SUMMARY OF THE INVENTION

Pharmaceutical compositions comprising two or more anticancer agents encapsulated in a vesicle, wherein the molar ratio of the agents provides a synergistic therapeutic effect, are described herein. Preferably the vesicle is a liposome. Methods of making and using the pharmaceutical compositions are further described.

The pharmaceutical compositions contain two or more therapeutically active agents encapsulated within the same vesicle at a molar ratio which provides a synergistic therapeutic effect compared to delivering each of the agents alone. The therapeutic agents include nucleobases, nucleobase analogues, or combinations thereof, co-encapsulated with anthracyclines or co-encapsulated with other nucleobases or other nucleobase analogues. The two or more agents encapsulated within the same vesicle can be delivered to a patient in need of treatment, such as a tumor in a cancer patient. In some embodiments, the agents are encapsulated in separate vesicles and delivered simultaneously.

The vesicle is preferably a liposome. In preferred embodiments, the liposome contains a cationic lipid, is positively charged, and/or has a positive zeta potential. In further embodiments, the liposome is coated with a water-soluble, biocompatible polymer, preferably a polyalkylene oxide. In embodiments wherein the liposome is coated with a polyalkylene oxide, the zeta potential of the coated liposome can be negative. In some embodiments, the polyalkylene oxide is polyethylene glycol. In some embodiments, the polyalkylene oxide is physically adsorbed to the surface of the liposome. In preferred embodiments, the polyalkylene oxide is covalently attached to a lipid molecule in the liposome. For instance, PEG is incorporated as a chemical conjugate to a lipid, preferably DSPE (1,2-Distearoyl-sn-glycero-3-phosphoethanolamine), which is further physically embedded in the lipid membrane.

In some embodiments, the nucleobase analogue includes 5-fluorouracil. In further embodiments, the nucleobase analogue includes 5-fluorouridine in which one or more hydroxyl groups of the ribosyl moiety have been esterified with one or more tryptophan residues, preferably three tryptophan residues.

The compositions can be formulated for any suitable method of administration. Suitable dosage forms for parenteral administration include, but are not limited to, solutions, suspensions, and emulsions. Suitable oral dosage forms include, but are not limited to, tablets, capsules, solutions, suspensions, emulsions, syrups, and lozenges. Suitable dosage forms for intranasal administration include, but are not limited to, solutions, suspensions, and emulsions. Optionally, the compositions can be administered to and through a mucosal site.

Also described is a method for synthesizing nucleobase analogues. The method involves a chemical reaction between a nucleophile on a nucleobase or nucleobase analogue and an N-carboxyanhydride (NCA) compound. The nucleobase analogue can be a nucleoside or a deoxynucleoside. The nucleobase analogue can be 5-fluorouridine, 2'-deoxy-5-fluorouridine, 2', 3'-dideoxy-5-fluorouridine; preferably the nucleobase analogue is 5-fluorouridine. The NCA compound includes a substituted or unsubstituted non-aromatic hydrophobic group, a substituted or unsubstituted aryl group, a substituted or unsubstituted heteroaryl group, or a combination thereof. The nitrogen atom in the atoms that form the NCA group can be protected or unprotected with a protecting group. Preferably, the nitrogen atom in the NCA group is protected. In preferred embodiments, the NCA is Boc-protected tryptophan-N-carboxyanhydride, in which the nitrogen atom in the NCA group is protected with Boc. This approach does not require the presence of an activating reagent, such as N,N'-diisopropylcarbodiimide, due to the presence of the NCA group, and generally gives higher nucleobase analogue yields compared to approaches that use an activating reagent.

The compositions are effective at treating a variety of cancers.

BRIEF DESCRIPTION OF THE DRAWINGS

FIGS. 2A and 2B. FIG. 2A is a bar graph of the Combination Indices calculated for various ratios of 5FU+DOX exposed to BT-474 human breast cancer cells. For all ratios, 5FU concentration was kept constant at 487 µM. Data expressed as mean±SD (n≥8). FIG. 2B is a bar graph of the ratio of $D_{50}$ for BT-474 cells relative to MCF 10A breast epithelial cells for 5FU (black bars) and DOX (white bars) treated as single drugs or in combinations of R-819 (synergistic ratio), R=6551 (antagonistic ratio). $D_{50}$s were determined for experimental fits of cell inhibition data to the ME model, and error is propagated from the standard error of the model fit.

FIGS. 3A-3F are graphs comparing fractional cell inhibition for 5FU+DOX in the synergistic ratio R=819±64 (squares) or antagonistic ratio R=6551±170 (triangles). FIG. 3A shows fractional cell inhibition based on exposure of BT-474 human breast cancer cells to DOX alone (circles), compared to exposure to a synergistic ratio (squares) and an antagonistic ratio (triangles) of 5FU+DOX. FIG. 3B shows fractional cell inhibition based on exposure of BT-474 human breast cancer cells to 5FU alone (circles), compared to exposure to a synergistic ratio (squares) and an antagonistic ratio (triangles) of 5FU+DOX. FIG. 3C shows fractional cell inhibition based on exposure of bEnd.3 mouse brain endothelial cells to DOX alone (circles), compared to exposure to a synergistic ratio (squares) and an antagonistic ratio (triangles) of 5FU+DOX. FIG. 3D, shows fractional cell inhibition based on exposure of bEnd.3 mouse brain endothelial cells to 5FU alone (circles), compared to exposure to a synergistic ratio (squares) and an antagonistic ratio (triangles) of 5FU+DOX. FIG. 3E shows fractional cell inhibition based on exposure of MCF 10A human breast epithelial cells to DOX alone (circles), compared to exposure to a synergistic ratio (squares) and an antagonistic ratio (triangles) of 5FU+DOX. FIG. 3F shows fractional cell inhibition based on exposure of MCF 10A human breast epithelial cells to 5FU alone (circles), compared to exposure to a synergistic ration (squares) and an antagonistic ratio (triangles) of 5FU+DOX. Cell growth inhibition was evaluated via MTT cytotoxicity assays. Single drug treatments of DOX (top, circles) and 5FU (bottom, circles) are shown for comparison. Dashed lines represent fits to the ME model. Data expressed as mean±SD (N≥6).

FIGS. 4A and 4B. FIG. 4A shows in vitro cell growth inhibition of BT-474 cells exposed to free DOX (circles), DOX in neutral liposomes (triangles), and DOX in cationic liposomes (squares) for 72 hrs. Data expressed as mean±SD (N≥6). Dashed lines represent dose-effect curves fit to the ME model, with $D_{50}$ concentrations of DOX, DOX-L and +DOX-L corresponding to 0.3 µM, 33.5 µM, and 6.7 µM, respectively. FIG. 4B shows DOX fluorescence (black) intensity is reported as mean±SD (N=3). Representative images are shown as an average of 10 µm z-stacks. Scale bar=20 µm. *, P<0.05; **, P<0.01 performed by two-tailed Student's t-test.

FIGS. 5A and 5B. FIG. 5A shows in vitro activities of the ribonucleoside analogue of 5FU (5FUR) (open squares) and tryptophan-modified 5FUR (5FURW) (filled squares) in free solution. FIG. 5B shows in vitro activities of the ribonucleoside analogue of 5FU (5FUR) (open squares) and tryptophan-modified 5FUR (5FURW) (filled squares) in liposomes. Data shown as average±SD (N=6).

FIGS. 6A, 6B, 6C, and 6D. FIG. 6A shows CIs for 5FUR+DOX (hatched bars) or 5FURW+DOX (black bars). BT-474 cells were exposed to various ratios of each combination for 72 hours. Drug concentrations for 5FUR and DOX, respectively, corresponding to each ratio were: 0.1 (0.06, 0.60), 0.5 (0.15, 0.3), 1.0 (0.3, 0.3), 5.0 (1.5, 0.3), 19 (2.8, 0.15), 75 (11.25, 0.15), 150 (22.5, 0.15), 300 (22.5, 0.075), 600 (45, 0.075). Drug concentrations for 5FURW and DOX, respectively, corresponding to each ratio were: 0.1 (0.06, 0.60), 0.5 (0.15, 0.30), 1 (0.30, 0.30), 5 (1.50, 0.30), 19 (5.60, 0.30), 75 (22.50, 0.30), 150 (45.00, 0.30), 300 (45.00, 0.15), 600 (90.0, 0.15). FIG. 6B shows the toxicity of free tryptophan (W) incubated with 4T1 (circles) or BT-474 (squares) cells. FIG. 6C shows the toxicity of liposome-encapsulated W incubated with 4T1 (circles) or BT-474 (squares) cells. Cells were incubated with W concentrations expected to be present during 5FURW cytotoxicity assays. Data expressed as mean±SD (N=6). FIG. 6D shows CIs calculated for various ratios of 5FURW-L and +DOX-L exposed to BT-474 cells for 72 hours. Drug concentrations for 5FURW and DOX, respectively, corresponding to each ratio were: 0.1 (0.30, 2.40), 0.5 (0.60, 1.20), 1 (1.20, 1.20), 5 (22.50, 4.70), 19 (45.00, 2.40), 75 (180.00, 2.40), 150 (180.00, 1.20), 300 (180.00, 0.60), 600 (360.00, 0.60). Data shown as average±SD (N≥6).

FIGS. 7A, 7B and 7C. 4T1 cancer cell growth inhibition by various 5FURW- and DOX-co-encapsulated liposomes. FIG. 7A shows a comparison of 5FURW-liposomes (open circles) to antFD-L (R=12.2, filled circles), synFD-L (R=0.18, filled squares), and synPFD-L (R=0.15, filled diamonds). FIG. 7B shows a comparison of the same co-loaded liposomes in FIG. 7A with DOX-liposomes (open circles). Dashed lines represent fits to the ME model. Average calculated CI for the cell inhibition data of antFD-L and synFD-L are 1.92±1.21 and 0.31±0.24, respectively. Data reported as average±SD (N≥6). FIG. 7C shows drug release of 5FURW (squares) and DOX (circles) from synPFD-L in PBS at pH 5.5 (open marks) or pH 7.4 (closed marks). Data shown as average±SD (N=3). Lines represent exponential fits to release profiles ($t_{1/2}$, =14.1, 27.7, 26.9, and 35.3 for 5FURW pH 5.5, 5FURW pH 7.4, DOX pH 5.5, and DOX pH 7.4, respectively).

FIGS. 8A-8E. FIG. 8A shows 4T1 tumor volumes of untreated BALB/c mice (circles), mice treated with synPFD-L (squares), or free 5FURW and DOX in saline (triangles) at drug-equivalent doses of about 0.61 mg/kg 5FURW and 3 mg/kg DOX (R=0.15). Mice were injected via i.v. tail vein on Days 3, 5, 7, and 9 post-tumor inoculation. Data shown as mean±SEM (N=8 except for last two points of control, where N≥5). Significance is provided for Day 23 data points, where untreated mice survival>50%. FIG. 8C shows percent survival of untreated BALB/c mice (circles), mice treated with synPFD-L (squares), or free 5FURW and DOX in saline (triangles). FIG. 8B shows the corresponding body weight changes of the tumor-bearing mice of FIGS. 8A and 8C. FIG. 8D shows tumor volume progression of each mouse treated with synPFD-L. Mice with complete tumor eradication are indicated by filled marks, whereas mice with eventual normal tumor growth are represented as open marks. FIG. 8E shows the biodistribution of $^3$H-synPFD-L after 6 hours post i.v. tail injection. Data expressed as mean initial dose (ID) per g tissue±SEM (N=4).

FIG. 10A shows the in vitro toxicity of blank cationic liposomes against murine breast carcinoma cell line 4T1. FIG. 10B shows the in vitro toxicity of blank cationic liposomes against human breast cancer cell line BT-474. Data expressed as mean±SD (N=6). For all in vitro studies, non-toxic doses of <3 µmol/mL or <0.4 µmol/mL were utilized against BT-474 and 4T1 cell lines, respectively.

FIGS. 11A, 11B, and 11C show the dependence of 5FURW loading on pH, drug concentration, and encapsulation time, respectively.

FIGS. 12A, 12B, and 12C show the dependence of size and zeta-potential of 5FURW-loaded liposomes on pH, encapsulation time, and drug concentration, respectively.

FIGS. 13A and 13B show the viability of the 4T1 mouse and MDA-MB-231 human cancer cell lines as a function of drug concentration.

FIG. 14A is a graph of the ratios of 5FURW:DOX and the combination indices obtained from those ratios. FIG. 14B is a graph of the IC50 values of 5FURW and DOX used to complete the combination index calculations.

In FIG. 15A, 5FURW is added first, followed by the addition of DOX. In FIG. 15B, DOX is added first, followed by the addition of 5FURW.

DETAILED DESCRIPTION OF THE INVENTION

I. Definitions

Figure 1:
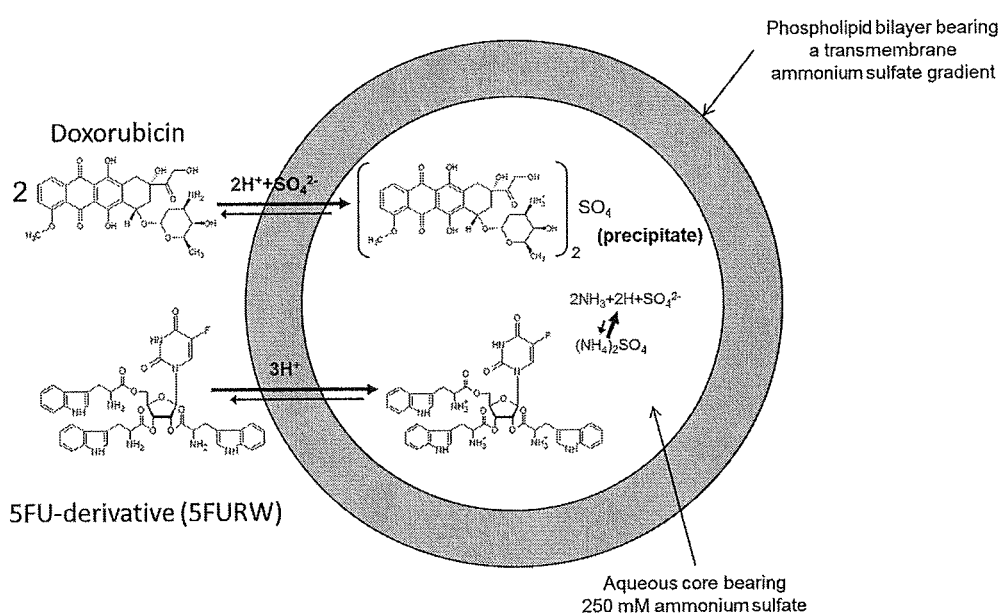
FIG. 1 is a schematic of a liposome with drugs encapsulated within an aqueous core.

"Hydrophobic" as used herein refers to substances that lack an affinity for water; tending to repel and not absorb water as well as not dissolve in or mix with water. Hydrophobicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in the organic solvent than in water, the compound is considered hydrophobic. For example, if the organic solvent is octanol, then a positive log P value indicates that the compound is hydrophobic.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms, such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Non-aromatic hydrophobic group" includes hydrophobic groups that do not have aromaticity. These include alkyl, substituted alkyl, alkenyl, substituted alkenyl, alkynyl, substituted alkynyl, alkoxy, substituted alkoxy, alkylthio, substituted alkylthio, cycloalkyls, substituted cycloalkyl, cycloalkenyls, substituted cycloalkenyls, cycloalkynyls, substituted cycloalkynyls. "Non-aromatic hydrophobic group" also includes hydrophobic amino acids that do not contain an aryl or a heteroaryl group. It is to be understood that the non-aromatic hydrophobic groups can be substituted with any of the substituents described above, with the proviso that the substituted non-aromatic hydrophobic group retains its hydrophobicity. The cyclic structures are formed from single or fused ring systems.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. Preferred cycloalkyls, cycloalkenyls, cycloalkynyls, heterocyclyls have from 3-10 carbon atoms in their ring structure, and more preferably have 5, 6 or 7 carbons in the ring structure.

"Aryl," and "aromatic" are used interchangeably, and refer to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, branched-chain alkyl, cycloalkyl (alicyclic), alkyl substituted cycloalkyl groups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are each independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —$NCOCOCH_2CH_2$; —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "treating" or "treatment", as used herein, indicates that the method has, at the least, mitigated abnormal cellular proliferation. For example, the method can reduce the rate of cancer growth in a patient, or prevent the continued growth of a cancer, or even reduce the overall reach of the cancer.

"Water soluble polymer", as used herein, means a polymer having a solubility of at least 1 mg/liter in water or monophasic aqueous-organic mixtures, at 37° C. and standard pressure.

As used herein "synergistic therapeutic effect" refers to a therapeutic effect that is greater than additive for the particular combination of drugs as determined using the combination index (CI) analysis.

As used herein, "activating reagent" refers to a compound that increases the reactivity of a functional group in another compound. For example, if the functional group is a carboxyl group (—C(O)OH), i can be activated by converting the —OH group into a group that can be more easily displaced (i.e., a good leaving group) in a nucleophilic substitution reaction compared to the —OH group. This effectively makes the activated compound into a good acyl donor. Exemplary activating reagents include: carbodiimides (e.g., N,N'-dicyclohexyl carbodiimides, N,N'-diisopropylcarbodiimide, 1-ethyl-3-(3-dimethylaminopropyl)carbodiimides) that can be used with dimethylaminopyridine; N,N-carbonyldiimidazole; and sulfonyl chlorides (e.g., p-toluene sulfonyl chloride and 5-isopropyl-2-methylbenzenesulfonyl chloride). Activating agents also include thionyl chloride and oxalyl chloride that convert the carboxyl group into an acyl chloride.

II. Pharmaceutical Compositions

A. Therapeutically Active Agents

The pharmaceutical compositions contain two or more therapeutically active agents encapsulated within a vesicle, the agents are present in a molar ratio that provides a synergistic therapeutic effect. The therapeutically active agent may be any drug providing a therapeutic or prophylactic effect in vivo. The drug is selected based on the disease or disorder to be treated or prevented.

Drugs contemplated for use in the pharmaceutical compositions described herein include, but are not limited to, the following categories and examples of drugs and alternative forms of these drugs such as alternative salt forms, free acid forms, free base forms, and hydrates:

anticancer agents (e.g. 5-fluorouracil and analogues thereof; gemcitabine; gemcitabine hydrochloride; cytarabine; decitabine; leucovorin; acivicin, aclarubicin, acodazole hydrochloride, acronine, adozelesin, aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; dacarbazine; dactinomycin; dexormaplatin; dezaguanine; dezaguanine mesylate; diaziquone; docetaxel; anthracyclines (such as doxorubicin, doxorubicin hydrochloride, epirubicin, epirubicin hydrochloride, idarubicin, idarubicin hydrochloride, valrubicin hydrochloride, daunorubicin, and daunorubicin hydrochloride); droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; flurocitabine; fosquidone; fostriecin sodium; hydroxyurea; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimus tine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogeinlanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospeanine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocannycin SA; ebselen; ecomustine; edelfosine; edrecolomab; eflornithine; elemene; emitefur; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B;

itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidasc; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosinc; superactivc vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribinc; trimetrexate; triptorelin; tropisetron; turosteridc; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanotcrone; zeniplatin; zilascorb; and zinostatin stimalamer; analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthamatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propranolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propranolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillamine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e g, aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds, hormones and hormone analogues (e.g., incretins and incretin mimetics such as GLP-1 and exenatide, androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, recombinantly produced insulin, insulin analogues, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); peptides; proteins (e.g., DNase, alginase, superoxide dismutase, and lipase); nucleic acids (e.g., sense or anti-sense nucleic acids encoding any therapeutically useful protein, including any of the proteins described herein, and siRNA); agents useful for erythropoiesis stimulation (e.g., erythropoietin); antiulcer/anti-reflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); oil-soluble vitamins (e.g., vitamins A, D, E, K, and the like); as well as other drugs such as mitotane, halonitrosoureas, anthrocyclines, and ellipticine.

The anticancer agents described above can be used in combination with another of the listed anticancer agents or another anticancer agent to provide a synergistic anticancer effect. Furthermore, any of the anticancer agents described above can be used in combination with another of the listed anticancer agents or another anticancer agent and with one or more agents from any of the other classes listed above to provide a synergistic anticancer effect.

A description of these and other classes of useful drugs and a listing of species within each class can be found in Martindale, *The Extra Pharmacopoeia*, 30th Ed. (The Pharmaceutical Press, London 1993), the disclosure of which is incorporated herein by reference in its entirety.

Anticancer Agents

In general, the pharmaceutical composition contains a combination of two or more anticancer agents, preferably at least one nucleobase or analogue thereof. Preferably, the nucleobase analogue includes the nucleobase that is substituted with a chemical moiety that includes a positively ionizable group or atom and optionally a substituted or unsubstituted non-aromatic hydrophobic group, a substituted or unsubstituted aryl group, a substituted or unsubstituted heteroaryl group, or combinations thereof. In some embodiments, the hydrophobic group is present, and is preferably an aromatic group.

The positively ionizable group can be (i) a substituent of or be included in a substituent that is attached (covalently or non-covalently) both to the substituted or unsubstituted non-aromatic hydrophobic group, a substituted or unsubstituted aryl group, a substituted or unsubstituted heteroaryl group, and to another moiety within the nucleobase analogue, (ii) a substituent of or be included in a substituent that is attached (covalently or non-covalently) only to the substituted or unsubstituted non-aromatic hydrophobic group, a substituted or unsubstituted aryl group, a substituted or unsubstituted heteroaryl group, and not to another moiety within the nucleobase analogue, (iii) a part of the main chain or cyclic core structure of the substituted or unsubstituted non-aromatic hydrophobic group, a substituted or unsubstituted aryl group, a substituted or unsubstituted heteroaryl group, or (iv) a combination of (i), (ii), and (iii).

In some embodiments the pharmaceutical composition contains a nucleobase analogue, optionally an analogue of 5FU, as the first anticancer agent and doxorubicin as the second anticancer agent. Preferred analogues of 5FU are prodrugs of 5FU, where the cleavable component provides similar chemical properties as DOX, such as amphipathicity, aromaticity and weak basicity.

In one embodiment, the nucleobase is represented by the formula:

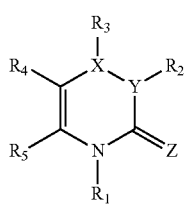

Formula I wherein X is carbon, Y is nitrogen and Z is oxygen, sulfur or NR', $R_1$, $R_2$, $R_3$, $R_4$ and $R_5$ are each independently hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, halogen, haloalkyl (such as $CF_3$, —$CH_2$—$CF_3$, —$CCl_3$), —CN, a polysaccharide, a substituted polysaccharide, a furanose, a substituted furanose, a deoxyfuranose (such as a deoxyribose), a substituted deoxyfuranose, a pyranose, a substituted pyranose, or a deoxypyranose, a substituted deoxypyranose, or NR'R", wherein R' and R" are each independently hydrogen, alkyl, substituted alkyl, alkenyl, substituted alkenyl, alkynyl, substituted alkynyl, aryl, substituted aryl, heteroaryl, substituted heteroaryl, polyaryl, substituted polyaryl, $C_3$-$C_{20}$ cyclic, substituted $C_3$-$C_{20}$ cyclic, heterocyclic, substituted heterocyclic, —$(CH_2)_m$—R''', wherein R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

In some embodiments, X, Y, Z, $R_1$, $R_3$, $R_4$ and $R_5$ are as defined above for Formula I, the bond between X and $R_3$ is a single bond, the bond between X and Y is a double bond, and $R_2$ is absent.

In some embodiments, X, Y, Z, $R_1$, $R_2$, $R_4$ and $R_5$ are as defined above for Formula I, the bond between X and $R_3$ is a double bond, the bond between X and Y is a single bond, and $R_3$ is oxygen, sulfur or NR', wherein R' is hydrogen, alkyl, substituted alkyl, alkenyl, substituted alkenyl, alkynyl, substituted alkynyl, aryl, substituted aryl, heteroaryl, substituted heteroaryl, polyaryl, substituted polyaryl, $C_3$-$C_{20}$ cyclic, substituted $C_3$-$C_{20}$ cyclic, heterocyclic, substituted heterocyclic, —$(CH_2)_m$—R''', wherein R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

In some embodiments, the nucleobases are as described above for Formula I, with the exception that at least one of $R_1$, $R_2$, $R_3$, $R_4$ and $R_5$, when present, contains a positively ionizable group or atom and a substituted or unsubstituted non-aromatic hydrophobic group, a substituted or unsubstituted aryl group, a substituted or unsubstituted heteroaryl group, or a combination thereof.

In some embodiments, Formula I describes analogues of 5-fluorouracil. For example, the nucleobase can have the formula:

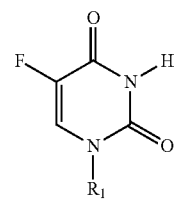

Formula VI wherein $R_1$ is a substituted alkyl, a furanose, a substituted furanose, a deoxyfuranose (such as a deoxyribose), a substituted deoxyfuranose, a pyranose, a substituted pyranose, a substituted deoxypyranose, or a deoxypyranose.

In some embodiments of Formula VI, $R_1$ is a substituted alkyl, wherein the substituents include a substituted or unsubstituted non-aromatic hydrophobic group, a substituted or unsubstituted aryl group, a substituted or unsubstituted heteroaryl group, or combinations thereof.

In some embodiments of Formula VI, $R_1$ is a substituted methyl, wherein the substituents include one or more hydrophobic amino acids, amino acids that include a heteroaryl side chain, or a combination thereof.

In some embodiments of Formula VI, $R_1$ is a substituted methyl, wherein the substituents are hydrophobic amino acids that include, but are not limited to, those represented by the formulae:

Formula II

Formula III wherein E is absent, or E is oxygen, sulfur, or $NR^{iv}$, wherein $R^{iv}$ is hydrogen, alkyl, substituted alkyl, alkenyl, substituted alkenyl, alkynyl, substituted alkynyl, aryl, substituted aryl, heteroaryl, substituted heteroaryl, polyaryl, substituted polyaryl, $C_3$-$C_{20}$ cyclic, substituted $C_3$-$C_{20}$ cyclic, heterocyclic, substituted heterocyclic, —$(CH_2)_m$—R''', wherein R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8, wherein R' and R" are as defined above. In further embodiments, E is oxygen, and R' and R" are each hydrogen.

One or more of the hydrogens in an alkyl group, such as a methyl group may be substituted to form a substituted alkyl (e.g. a substituted methyl). Optionally, the substituted alkyl or substituted methyl is substituted with one or more substituted or unsubstituted non-aromatic hydrophobic group, a substituted or unsubstituted aryl group, a substituted or unsubstituted heteroaryl group, or combinations thereof. For example, in a substituted methyl, one, two or three of the hydrogens may be each independently substituted with a substituted or unsubstituted non-aromatic hydrophobic group, a substituted or unsubstituted aryl group, a substituted or unsubstituted heteroaryl group, or combinations thereof. Preferably, in the case of the substituted methyl, only one of the hydrogens is substituted.

In some embodiments of Formula VI, $R_1$ is a furanose, a substituted furanose, a substituted deoxyfuranose, or a deoxyfuranose (such as a deoxyribose).

In some embodiments of Formula VI, $R_1$ is a substituted furanose or substituted deoxyfuranose.

In some embodiments of Formula VI, $R_1$ is a furanose, wherein the furanose is ribose, i.e., the nucleobase is 5-fluorouridine.

In some embodiments of Formula VI, $R_1$ is a substituted furanose, wherein the substituents include a substituted or unsubstituted non-aromatic hydrophobic group, a substituted or unsubstituted aryl group, a substituted or unsubstituted heteroaryl group, or a combination thereof.

In some embodiments of Formula VI, $R_1$ is a substituted furanose, wherein the substituents include hydrophobic amino acids, amino acids that include a heteroaryl side chain, or a combination thereof.

In some embodiments of Formula VI, $R_1$ is a substituted furanose, wherein the substituents include hydrophobic amino acids, wherein the hydrophobic amino acids include, but are not limited to those represented by the formulae:

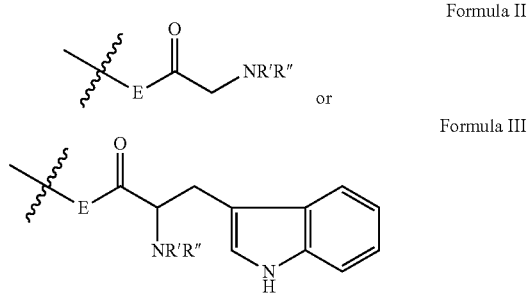

Formula II

Formula III wherein E is absent, or E is oxygen, sulfur, or $NR^{iv}$, wherein $R^{iv}$ is hydrogen, alkyl, substituted alkyl, alkenyl, substituted alkenyl, alkynyl, substituted alkynyl, aryl, substituted aryl, heteroaryl, substituted heteroaryl, polyaryl, substituted polyaryl, $C_3$-$C_{20}$ cyclic, substituted $C_3$-$C_{20}$ cyclic, heterocyclic, substituted heterocyclic, —$(CH_2)_m$—''', wherein R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8, wherein R' and R" are as defined above. In further embodiments, E is absent, and R' and R" are each hydrogen.

In some embodiments of Formula VI, the nucleobases have the structures shown below:

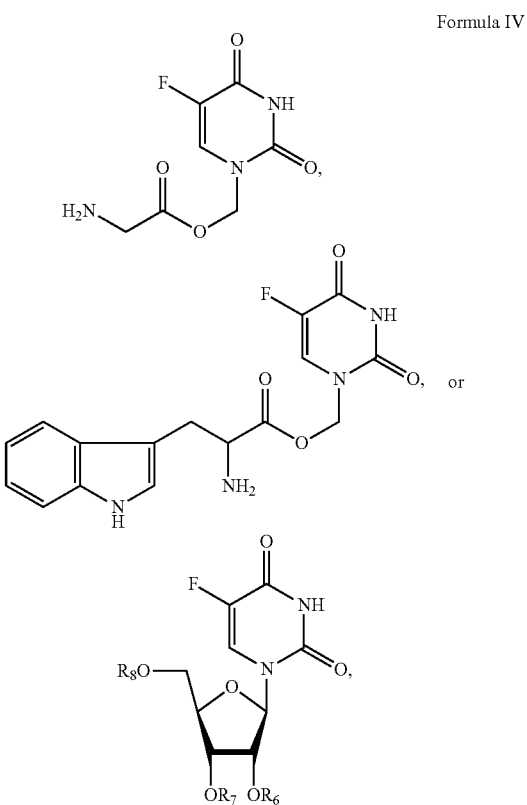

wherein $R_6$, $R_7$ and $R_8$ are each independently hydrogen or Formula III, wherein E is absent, wherein at least one of $R_6$, $R_7$ or $R_8$ is Formula III, wherein E is absent. In preferred embodiments $R_6$, $R_7$ and $R_8$ are Formula III, wherein R' and R" are hydrogen. In some embodiments, the nucleobases can be 1-[(aminomethyl)-ester]methylene-5-fluorouracil (5FUG), tryptophan 5-fluorouracil ester or (5-fluoro-2,4-dioxo-3,4-dihydropyrimidin-1(2H)-yl)methyl tryptophanate (5FUW), 5-fluorouridine-2', 3', 5'-trityptophanate (5FURW), a combination thereof.

Although the embodiments described above for Formula VI have fluorine as $R_4$, it should be understood that the fluorine can be substituted with any other halogen.

In one embodiment, the pharmaceutical composition contains a combination of two or more anticancer drugs, preferably at least nucleobase represented by the formula:

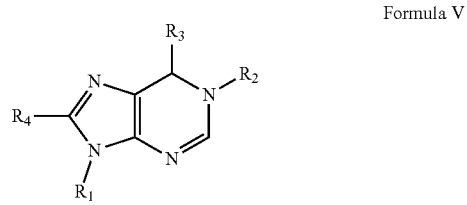

Formula V wherein Z is oxygen, sulfur or NR', wherein R' is hydrogen, alkyl, substituted alkyl, alkenyl, substituted alkenyl, alkynyl, substituted alkynyl, aryl, substituted aryl, heteroaryl, substituted heteroaryl, polyaryl, substituted polyaryl, $C_3$-$C_{20}$ cyclic, substituted $C_3$-$C_{20}$ cyclic, heterocyclic, substituted heterocyclic, —$(CH_2)_m$—R''', wherein R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8, wherein $R_1$, $R_2$, $R_3$, and $R_4$ are each independently hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, halogen, haloalkyl (such as $CF_3$, —$CH_2$—$CF_3$, —$CCl_3$), —CN, a polysaccharide, a substituted polysaccharide, a furanose, a substituted furanose, a deoxyfuranose (such as a deoxyribose), a substituted deoxyfuranose, a pyranose, a substituted pyranose, a deoxypyranose, a substituted deoxypyranose, or NR'R'', wherein R' and R'' are each independently hydrogen, alkyl, substituted alkyl, alkenyl, substituted alkenyl, alkynyl, substituted alkynyl, aryl, substituted aryl, heteroaryl, substituted heteroaryl, polyaryl, substituted polyaryl, C3-C20 cyclic, substituted C3-C20 cyclic, heterocyclic, substituted heterocyclic, —(CH2)m-R''', wherein R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

In some embodiments, Z, $R_1$, $R_3$, $R_4$ and $R_5$ are as defined above for Formula V, the bond between X and $R_3$ is a single bond, the bond between X and Y is a double bond, and $R_2$ is absent.

B. Vesicles

The combination of agents is encapsulated in a vesicle. Preferred vesicles are liposomes. Suitable methods, materials and lipids for making liposomes are known in the art. Liposome delivery vehicles are commercially available from multiple sources. Liposomes can be formed from a single lipid bilayer (i.e., the liposome can be unilamellar) or several concentric lipid bilayers (i.e., the liposome can be multilamellar). The liposome may be formed from a single lipid; however, in some embodiments, the liposome is formed from a combination of more than one lipid. The lipids can be neutral, anionic or cationic at physiologic pH. In preferred embodiments, the liposome is a bilayer that is cationic.

A schematic of a liposome with drugs encapsulated within an aqueous core is shown in FIG. 1. As shown in FIG. 1, the liposomes contain a phospholipid bilayer, typically with a transmembrane ammonium sulfate gradient.

Typical lipids that can be used to faun the liposomes include, but are not limited to cationic, zwitterionic, and PEGylated anionic lipids. Preferably the cationic lipid is DOTAP (1,2-dioleoyl-3-trimethylammonium-propane), zwitterionic lipid is DSPC (1,2-Distearoyl-sn-glycero-3-phosphocholine), and the PEGylated anionic lipid is PEG2000-DSPE (1,2-distearoyl-sn-glycero-3-phosphoethanolamine-N-[methoxy(polyethylene glycol)-2000]). Preferably, the molar ratio of lipids is 75:5:10:10 DSPC:PEG2000-DSPE:DOTAP:Cholesterol.

Despite the use of liposomes for chemotherapy delivery since 1995, overall response rates have not significantly improved compared to free drug administration (O'Brien, et al., Annals of Oncology 2004, 15(3), 440-449; Jehn, et al., Anticancer Research 2008, 28(6B), 3961-3964). Second generation liposomes, such as those described herein not only significantly improve therapeutic efficacy of free chemotherapy administrations, but also maintain the safety benefit of liposomal formulations.

For formulations containing 5FU and DOX, the liposomes may be formed from a mixture of cationic, zwitterionic, and PEGylated anionic lipids in a preferable molar ratio of 75:5:10:10 zwitterionic:PEGylated anionic:cationix:Cholesterol.

In a preferred embodiment, 5FURW and DOX are encapsulated in a liposome containing 1,2-Distearoyl-sn-glycero-3-phosphocholine (DSPC), 1,2-dioleoyl-sn-glycero-3-phosphoethanolamine-N-[methoxy(polyethylene glycol)-2000] (mPEG-DSPE), 1,2-dioleoyl-3-trimethylammonium-propane (DOTAP), and cholesterol (Chol) in a molar ratio ranging from of 55-80:1-20:1-40:1-40 (DSPC:mPEG-DSPE:DOTAP:Chol). In preferred embodiments, 5FURW and DOX are encapsulated in a liposome containing the phospholipids in a molar ratio of 75:5:10:10 (DSPC:mPEG-DSPE:DOTAP:Chol).

In some embodiments, the liposomes are coated with a water-soluble, biocompatible polymer. Suitable polymers include, but are not limited to polyalkylene oxides such as polyethylene glycol (PEG), polyethylene glycol-polypropylene block copolymer such as a PLURONIC®, poly(N-isopropylacrylamide) (PNIPAM), polyacrylamide (PAM), poly(carboxybetaine) (pCB), poly(sulfobetaine) (pSB), and polyethyleneimine (PEI).

The polymers typically have a molecular weight of 1,000 to 1,000,000 Daltons, preferably 10,000 to 1,000,000 Daltons. In one embodiment, the polymer is hydrolytically degradable. In preferred embodiments, the polymer is polyethylene glycol forming coated liposomes collectively known as PEGylated liposomes.

C. Ratios of Therapeutically Active Agents

The relative amount of each therapeutically active agent in the pharmaceutical composition is selected to provide a synergistic effect when the combination of the drugs is delivered together in the formulation. Suitable ratios of the active agents in the formulation for providing a synergistic effect can be determined using Chou and Talalay's Combination Index (CI) (Chou, T. C., Pharmacol Rev, 2006. 58(3): p. 621-81). In this analysis, the active agents of interest are combined in a variety of molar ratios (R) to assess for synergy.

The combination index (CI) theorem offers a quantitative definition for additive effect (CI=1), synergism (CI<1), and antagonism (CI>1) in drug combinations, where synergism is more than an additive effect and antagonism is less than an additive effect.

For example, for a formulation containing two drugs, the derived combination index equation is:

$$CI = \frac{(D)_1}{(D_x)_1} + \frac{(D)_2}{(D_x)_2} = \frac{(D)_1}{(D_m)_1[f_a/(1-f_a)]^{\frac{1}{m1}}} + \frac{(D)_2}{(D_m)_2[f_a/(1-f_a)]^{\frac{1}{m2}}} \quad \text{Eq. 1}$$

In Equation I, D is the dose (or concentration of a drug); $f_a$ is fraction affected by D and can be used to describe, for example, fractions of cells whose growth was inhibited, fractional tumor volume reduction or other drug targets which were inhibited due to drug exposure; $D_m$ is the median-effect dose (e.g., $IC_{50}$); and m is the coefficient signifying the shape of the dose-effect relationship. $(Dx)_1$ is for $(D)_1$ "alone" that inhibits a system x %, and $(Dx)_2$ is for $(D)_2$ "alone" that inhibits a system x % whereas in the numerator, $(D)_1+(D)_2$, "in combination" also inhibit x %. Note that the denominators of the last two terms are the expression of the median-effect equation (MEE).

The CI Value quantitatively defines synergism (CI<1), additive effect (CI=1) and antagonism (CI>1).

Molar ratios can be derived from in vitro and in vivo experiments. For example, the molar ratio (R) of 5FU:DOX was assessed in vitro in BT-474 human breast cancer cells. The greatest synergy was observed when R=819:1±64. At this ratio, CI was less than 1.

D. Targeting Agents

In some embodiments, the vesicles include one or more targeting agents that recognize one or more targets associated with a particular organ, tissue, cell or subcellular locale. The targeting agents are attached covalently or non-covalently to the surface of the vesicle. In some embodiments, the targeting agents are covalently attached directly or indirectly through a linker to the surface of the vesicle. In some embodiments, the targeting agents are non-covalently attached to the surface of the vesicle, through charge interactions, affinity interactions, metal coordination, physical adsorption, host-guest interactions, hydrophobic interactions, pi-stacking interactions, hydrogen bonding interactions, van der Waals interactions, magnetic interactions, etc. The targeting agent can be a protein, peptide, nucleic acid, saccharide, polysaccharide, organic molecule, or combinations thereof.

E. Dosage Forms

The pharmaceutical compositions can be in any suitable form for administration. In some embodiments, the dosage form is a parenteral dosage form. In certain embodiments, the compositions are administered locally, for example, by injection directly into a site to be treated (e.g., into a tumor). In others, the pharmaceutical composition is provided in an enteral dosage form. Suitable oral dosage forms include, but are not limited to, tablets, capsules, solutions, suspensions, emulsions, syrups, and lozenges. Suitable dosage forms for transmucosal administration (intranasal, vaginal, rectal, or sublingual) include but are not limited to, solutions, suspensions, and emulsions.

a. Parenteral Dosage Forms

Suitable parenteral dosage forms include, but are not limited to, solutions, suspension, and emulsions. In some embodiments, the pharmaceutical composition is injected directed at the tumor site.

Formulations for parenteral administration may contain one or more pharmaceutically acceptable excipients including, but not limited to, surfactants, salts, buffers, pH modifying agents, emulsifiers, preservatives, anti-oxidants, osmolality/tonicity modifying agents, and water-soluble polymers.

The emulsion is typically buffered to a pH of 3-8 for parenteral administration upon reconstitution. Suitable buffers include, but are not limited to, phosphate buffers, acetate buffers, and citrate buffers.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium azide, sodium benzoate, sodium propionate, benzalkonium chloride, benzethonium chloride, benzyl alcohol, cetypyridinium chloride, chlorobutanol, phenol, phenylethyl alcohol, and thimerosal.

b. Dosages

Suitable dosages for each formulation can be determined by known methods.

Optionally, the formulations deliver low doses of the chemotherapeutics. Low doses as referred to herein means cumulative chemotherapy doses of less than or equal to 15 mg/kg.

Commonly low doses of chemotherapeutics have been regarded as inactive. However, as shown by the Examples herein, low dose chemotherapy elicited remarkable tumor disappearance, when a synergistic ratio of 5FU+DOX was delivered to 4T1 cells in liposomes. Preferably, the formulation contains an effective amount of two or more chemotherapeutics in a synergistic ratio to deliver at least 3 mg/kg combined chemotherapy dose once every other day for at minimum 4 injections to a patient in need thereof.

Suitable dosages for parenteral formulations containing combination of at least one nucleobase or analogue thereof and at least anthracycline encapsulated within a liposome range between about 0.01 mg of the nucleobase/mL and about 5 mg of the nucleobase/mL, optionally between 0.1 and 1.5 mg of the nucleobase/mL, and between about 0.05 mg of the anthracycline/mL and about 10 mg of the anthracycline/mL, optionally between about 1 mg of the anthracycline/mL and about 5 mg of the anthracycline/mL. In preferred embodiments, the formulation contains a liposome with the agents to be delivered encapsulated therein. Preferably, the nucleobase in the liposome formulation is a 5FU analogue, such as 5FURW (5-fluorouridine in which the three hydroxyl groups of the ribose unit are esterified with tryptophan) and the anthracycline in the liposome formulation is doxorubicin.

In some embodiments, the dose of the nucleobase analogue, such as 5FURW, in the liposome formulation is about 0.61 mg/mL, and the dose of the anthracycline, such as doxorubicin, in the liposome formulation is about 1.64 mg/mL.

III. Methods of Manufacture

The nucleobase analogues can be synthesized by chemically modifying a nucleobase to include one or more nucleophilic atoms, followed by esterification of the one or more nucleophilic atoms with a desired organic group. In some aspects, one or more nucleophilic secondary amines of a nucleobase, such as 5-fluorouracil, react with a carbonyl group in another compound to form a carbinolamine. The hydroxyl group of the carbinolamine can be esterified with an organic compound that includes a carboxylic acid group, optionally in the presence of an activating reagent, such as N,N'-diisopropylcarbodiimide. In some aspects, the compound that includes the carbonyl group can be an aldehyde or ketone. In some aspects, the aldehyde can be formaldehyde.

In some aspects, the nucleobase analogues can be synthesized directly from a nucleoside, such as 5-fluorouridine, or deoxynucleoside, such as 2'-deoxy-5-fluorouridine, via esterification of one or more hydroxyl groups in the sugar unit of the nucleoside or deoxynucleoside with an organic compound that includes a carboxylic acid group, optionally in the presence of an activating reagent, such as N,N'-diisopropylcarbodiimide.

For the approaches described above, the organic compound that includes the carboxylic acid group can be a compound that also includes a substituted or unsubstituted non-aromatic hydrophobic group, a substituted or unsubstituted aryl group, a substituted or unsubstituted heteroaryl group, or a combination thereof. The carboxylic acid-containing compound can be protected or unprotected. In some aspects, the compound that includes the carboxylic acid group can be an amino acid. In some aspects, the amino acid can be tryptophan, phenylalanine, tyrosine, histidine, or a combination thereof. Preferably, the amino acid is protected with a protecting group such as Boc. After the reaction, the protecting group can be removed with a suitable reagent. For instance Boc can be removed using trifluoroacetic acid.

In some aspects, the nucleobase analogues can be synthesized directly from the reaction of a nucleoside, such as 5-fluorouridine, or deoxynucleoside, such as 2'-deoxy-5-fluorouridine, with another organic compound that includes one or more NCA groups, in the absence of an activating reagent. The compound that includes the one or more NCA groups can also include a substituted or unsubstituted non-aromatic hydrophobic group, a substituted or unsubstituted aryl group, a substituted or unsubstituted heteroaryl group, or a combination thereof. The nitrogen atom in the atoms that form the one or more NCA groups can be protected or unprotected with a protecting group. Preferably the nitrogen atom in the one or more NCA groups is protected. The NCA containing compound can be an amino acid. In preferred embodiments, the amino acid containing the NCA group is tryptophan-N-carboxyanhydride, phenylalanine-N-carboxyanhydride, tyrosine-N-carboxyanhydride, histidine-N-carboxyanhydride, or a combination thereof, in which the nitrogen atom in the NCA group is protected with a protecting group, such as Boc. After the reaction, the protecting group can be removed with a suitable reagent. For instance, Boc can be removed using trifluoroacetic acid.

The compositions described herein typically encapsulate the anticancer agents, or analogues thereof within a liposome, and optionally coat the liposome with a water-soluble, biocompatible polymer. For example, the agents may be incubated with liposomes after generation of the transmembrane ammonium sulfate gradient. Preferably the water-soluble, biocompatible polymer is a polyalkylene oxide. In embodiments wherein the liposome is coated with a polyalkylene oxide, the zeta potential of the coated liposome is negative, positive, or neutral. In some embodiments, the polyalkylene oxide is polyethylene glycol. In some embodiment, the polyalkylene oxide is physically adsorbed to the surface of the liposome. In preferred embodiments, the polyalkylene oxide is covalently attached to a lipid molecule in the liposome.

The water-soluble, biocompatible polymer can be terminated with an alkoxy group (such as a methoxy group), an amine group, or a carboxyl group.

In some embodiments, the drug is incorporated in an organic phase, prior to the lipid film formation, if the agent displays poor water solubility.

In other embodiments, the agent is introduced in the ammonium sulfate film hydration solution upon vesicle formulation.

In yet other embodiments, a first agent is incubated initially with liposomes after generation of the transmembrane ammonium sulfate gradient for 2 hours, followed by incubation of the second agent. Free drug is removed by a suitable method. For example, the liposomes may be passed through a Sephadex G-25 PD-10 column to remove free drug.

IV. Methods of Use and Administration

The compositions described herein can be used to treat cancer in a patient. Cancers to be treated include, but are not limited to, breast cancer (e.g., metastatic or locally advanced breast cancer), prostate cancer (e.g., hormone refractory prostate cancer), renal cell carcinoma, lung cancer (e.g., small cell lung cancer and non-small cell lung cancer (including adenocarcinoma, squamous cell carcinoma, bronchoalveolar carcinoma and large cell carcinoma)), pancreatic cancer, gastric cancer (e.g., gastroesophageal, upper gastric or lower gastric cancer), colorectal cancer, squamous cell cancer of the head and neck, ovarian cancer (e.g., advanced ovarian cancer, platinum-based agent resistant or relapsed ovarian cancer), lymphoma (e.g., Burkitt's, Hodgkin's or non-Hodgkin's lymphoma), leukemia (e.g., acute myeloid leukemia) and gastrointestinal cancer.

In one embodiment, following administration of the composition, the adverse side effects are reduced compared to the delivery of the same amount of a combination of topoisomerase I and II inhibitors in an unconjugated form. In some embodiments, the adverse side effect that is reduced is hematological toxicity.

EXAMPLES

The present invention may be further understood by reference to the following non-limiting examples.

Example 1. Investigating Drug Ratio Suitable for Synergy and Encapsulation of Drugs into Liposomes Materials and Methods (i) Cell Culture All cell lines were obtained by ATCC and maintained in a humidified $CO_2$ incubator at 37° C. BT-474 human breast cancer cells were cultured in Hybri-Care medium (ATCC) supplemented with 10% fetal bovine serum (FBS; Thermo Scientific), and 4T1 murine breast cancer cells were cultured in RPMI-1640 medium (Thermo Scientific) supplemented with 10% FBS and 1% penicillin/streptomycin (Thermo Scientific). MCF10A human breast epithelial cells were cultured in Mammary Epithelial Basal Medium (MEBM; Lonza) supplemented with BPE, hydrocortisone, hEGF, insulin, and 100 ng/mL cholera toxin (Sigma-Aldrich), and bEnd.3 mouse brain endothelial cells were cultured in Dulbecco's Modified Eagle's medium (DMEM; ATCC) supplemented with 10% FBS and 1% penicillin/streptomycin. For all experiments, cells were maintained in the exponential growth phase by subcultivation.

(ii) Chemotherapy Combination Studies

The Combination Index (CI) method (Chou, Pharmacological reviews 2006, 58(3), 621-621), was adopted to identify ratios of 5-fluorouracil (5FU; Sigma-Aldrich) and doxorubicin (DOX; LC laboratories) which synergistically inhibit cancer cell growth. For cell viability studies, BT-474 cells were seeded at a density of 10,000 cells per well in 100 μL cell culture medium, grown overnight and incubated with drug solutions for 72 hours. Cell viability was assessed post drug-incubation via 3-(4,5-Dimethylthiazol-2-yl)-2,5-diphenyltetrazolium bromide (MTT; Invitrogen Life Technologies) assays. Individual drug concentrations which inhibit 50% cell growth ($D_{50}$) were first determined by fitting dose-effect data to the median-effect model (Chou and Talalay, Advances in Enzyme Regulation 1984, 22, 27-55). For combinatorial studies, 5FU and DOX were simultaneously incubated with BT-474 cells at ratios of differing multiples of their $D_{50}$ concentrations, and cell viability was subsequently assessed. CI values were further calculated, as previously described (Chou, Pharmacological Reviews 2006, 58(3): p. 621-621), with the designations of CI<1, CI=1, and C>1 respectively representing synergy, additivity, and antagonism. The same methodology was applied to assess interactions between all other chemotherapy combinations presented.

(iii) Liposome Fabrication

Liposomes were fabricated utilizing the conventional thin film evaporation method (Szoka Jr, and Papahadjopoulos, Annual Review of Biophysics and Bioengineering 1980, 9(1), 467-508). Zwitterionic liposomes (DOX-L) were composed of 1,2-distearoyl-sn-glycero-3-phosphocholine (DSPC; Avanti Polar Lipids) and cholesterol (Chol; Sigma-Aldrich) in a molar ratio of 55:45, and cationic liposomes (+DOX-L, 5FU-L, 5FUG-L, 5FUW-L, 5FUR-L, 5FURW-L, 5FURWDOX-L) consisted of DSPC, 1,2-dioleoyl-3-trimethylammonium-propane (DOTAP; Avanti Polar Lipids), and Chol in a ratio of 80:10:10. PEGylated liposomes were prepared using DSPC:1,2-distearoyl-sn-glycero-3-phosphoethanolamine-N-[methoxy(polyethylene glycol)-2000] (mPEG-DSPE):DOTAP:Chol in a ratio of 75:5:10:10. Lipids were co-dissolved in chloroform and methanol in a round-bottom flask, and organic solvent was removed using a Buchi R-210 rotary evaporator at reduced pressure and 60° C. (5° C. above the lipid transition temperature) in order to form a thin lipid film. The film was subsequently hydrated in 125 mM ammonium sulfate at 60° C. and passed 21 times through an extruder (Avestin LiposoFast Extruder) with 100 nm polycarbonate filters. A transmembrane ammonium sulfate gradient was generated by passing liposomes through a Sephadex G-25 PD-10 column (GE Healthcare Life Sciences) equilibrated with PBS (Haran, et al., Biochimica et Biophysica Acta 1993, 1151(2), 201-15).

(iv) Liposome Characterization

To measure drug encapsulation, 50 μL of drug-loaded liposomes were dissolved in 950 μL methanol through vortexing and sonication. The dissolved liposomes were centrifuged at 12000 g for 20 minutes to allow the lipids to pellet. The supernatant was collected, diluted serially, and their absorbances were measured at 480 nm, 266 nm, 264 nm, 268 nm, 268 nm, and 394 nm to quantify DOX, 5FU, 5FUG, 5FUW, 5FUR, and 5FURW concentrations, respectively. Drug encapsulation is reported as the mol % of drug with respect to lipids±SD. Liposome sizes and ζ potentials were determined utilizing dynamic light scattering and electrophoretic light scattering, respectively, on a Malvern ZSizer Nano ZS. Samples were diluted 100× in distilled de-ionized water immediately prior analysis, and each measurement is reported as an average of 3 independent sets of at least 13 runs each ±SD.

(v) Liposomal Cancer Cell Growth Inhibition

In vitro anticancer efficacy of drug-loaded liposomes was determined via calcein-AM cell viability assay. BT-474 cells or 4T1 cells were seeded in a 96-well cell culture plate at a density of 11,000 cells per well or 1,000 cells per well in a total volume of 100 μL media and allowed to adhere overnight. Media was then replaced with fresh media containing liposomes and incubated for 72 hours or 48 hours for BT-474 or 4T1 cells, respectively. The discrepancies of cell seeding densities and drug incubation times between BT-474 cells and 4T1 cells is due to the much lower doubling time of 4T1 cells compared to BT-474. Parameters were modified such that untreated cells reached 70% confluency after treatment. After incubation with liposomes, media was aspirated and replaced with 1 μM calcein-AM in PBS for 30 minutes at room temperature. Fluorescence intensity of intracellularly hydrolyzed calcein-AM was measured using excitation and emission wavelengths of 490 nm and 520 nm. Fractional cell inhibition was calculated by subtracting fluorescence of live cells in experimental wells from those of untreated cells and normalizing against untreated cells. $D_{50}$ concentrations were determined by fitting experimental data to the median-effect model (Chou and Talalay, Advances in Enzyme Regulation 1984, 22, 27-55), and their error is reported as the standard error of the model fit.

(vi) Doxorubicin Internalization

Confocal laser scanning microscopy was utilized to visualize DOX intracellular distribution. BT-474 cells were seeded in an 8-well chambered borosilicate coverglass at 85,000 cells/well in a total cell culture medium volume of 300 μL/well, and were allowed to adhere overnight. Media was then replaced with fresh media containing DOX, DOX-L or +DOX-L at drug-equivalent concentrations of 1 μM, and cells were returned to 37° C. and 5% $CO_2$. After specified incubation times, cells were washed three times with warmed PBS, followed by nuclear staining with 25 μg/mL Hoechst for 30 minutes at 37° C. and 5% $CO_2$. Cells were washed three times with warmed PBS and then finally suspended in cell culture medium. Cells were immediately imaged live with an Olympus Fluoview 1000 spectral confocal microscope. Hoechst and DOX were excited by 405 nm 50 mW diode and a 488 nm 10 mW Argon gas lasers, respectively. Optical filters of 425-475 nm and 574-674 nm emission wavelengths were used to view fluorescence from Hoechst and DOX, respectively. Z-stacks were captured and analyzed as reported for ROS generation studies. Fluorescence intensity is reported as the raw integrated density of DOX fluorescence divided by number of cells, as determined by Hoechst labelling.

(vii) Synthesis of 5FU Analogues

Various 5FU prodrugs were synthesized to modify the native drug's chemical properties and facilitate incorporation in liposomes bearing a transmembrane ammonium sulfate gradient.

The preparation of 5FUG, 1-[(aminomethyl)-ester]methylene-5-fluorouracil, was performed similarly to the procedure presented by T. Ouchi and co-workers (Ouchi and Banba, Reactive Polymers 1992, 15, 153-163), as shown in Scheme 1.

Scheme 1

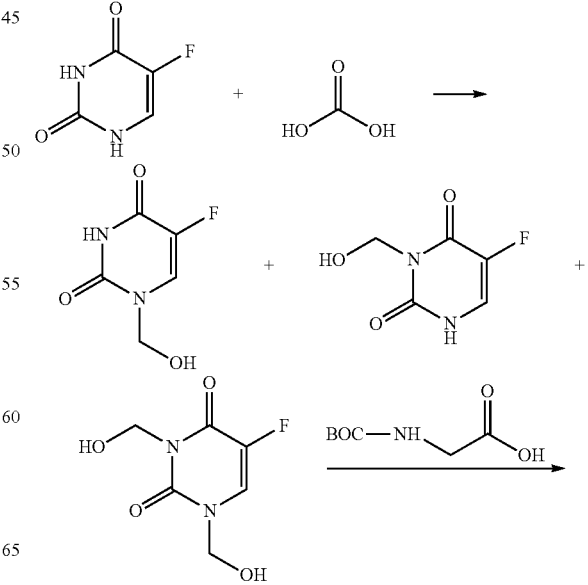

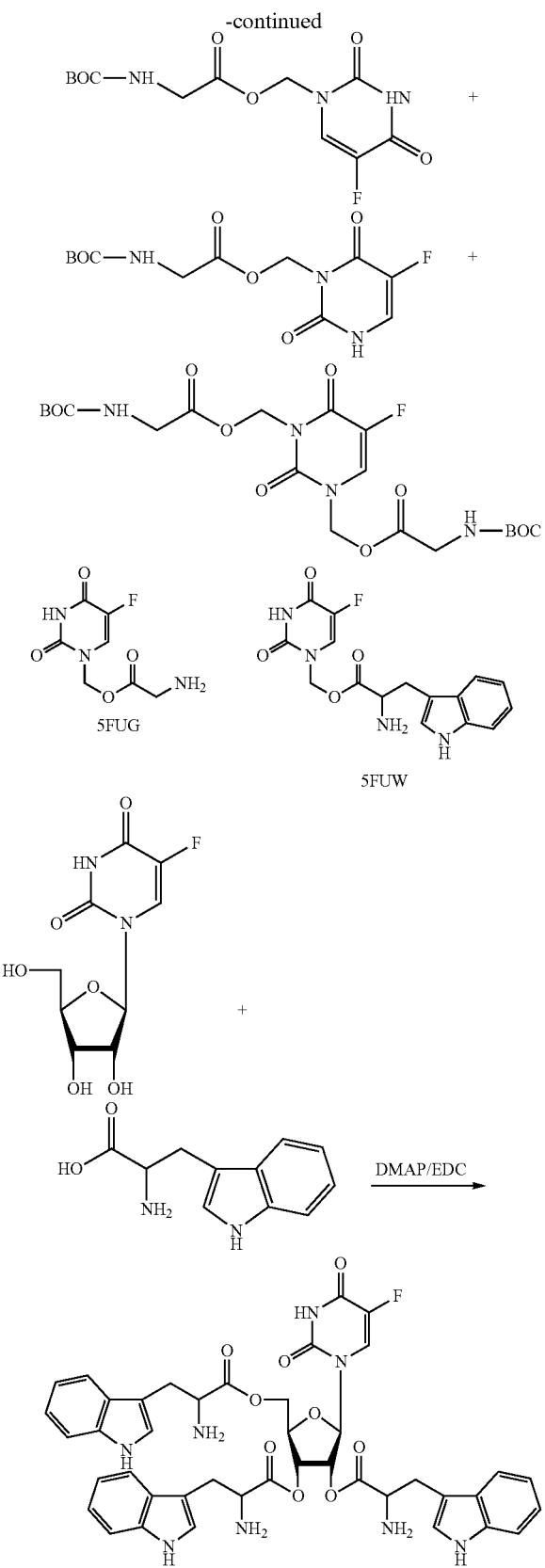

Briefly, 80 μL (1.07 mmol) of aqueous 37 w/w % formaldehyde was added to 100 mg (0.769 mmol) of 5FU and the reaction was kept at 60° C. overnight under mild stirring.

The resulting solution was then concentrated using a Buchi R-210 rotary evaporator at 45° C. and 30 mbar for 2 hours, to obtain a viscous oil comprising a mixture of three products (Scheme 1, first row). The hydroxymethyl-5FU (HMFU) contained therein was recrystallized with ethanol and dissolved in dry dimethyl sulfoxide (DMSO), to which 180 μL of N,N'-Diisopropylcarbodiimide (DIC; Sigma-Aldrich), 160 mg of N-(tert-Butoxycarbonyl)glycine (Boc-glycine; Sigma-Aldrich), and 190 mg of 4-(Dimethylamino) pyridine (DMAP; Sigma-Aldrich) were added. The reaction was allowed for 6 hours at room temperature under vigorous stirring to yield the products shown in Scheme 1, first and second rows. The solution was then copiously washed with 1N HCl and brine. The organic layer thus formed was dried with anhydrous sodium sulfate and evaporated to return an oily liquid. The 5FU-Glycine(Boc) was then precipitated and thoroughly washed with abundant ice-cold methyl isopropyl ether. To remove the Boc protection, 5FU-Glycine (Boc) was dissolved in 5 mL of 50% trifluoroacetic acid (TFA) in dichloromethane (DCM) and the solution stirred for 1 h at room temperature. The 5FUG was crystallized by evaporating the solvent and purified using Sep-Pack 2 mL C-18 columns (Waters), to separate the fraction containing the desired product (Scheme 1, third row).

5FUW, tryptophan 5-fluorouracil ester (Scheme 1, third row), was synthesized similarly. Tryptophan hydrochloride and 1-Ethyl-3-(3-dimethylaminopropyl)carbodiimide (EDC) were separately dissolved in dry DMSO in a proportion 1:1.1. The activated tryptophan was then added to the HMFU synthesized above, and allowed to react overnight at room temperature under mild stirring, to form an ester of tryptophan and HMFU. The product was precipitated in ice-cold water and the resulting crystals washed with acetone and dried. The 5FU-tryptophan ester was purified via reverse phase chromatography using SepPack C18 cartridges (Waters) and dried under vacuum.

The synthesis of 5FURW, tryptophan 5-fluorouridine ester, was achieved by mixing 5-Fluorouridine, tryptophan hydrochloride, and EDC in a proportion 1:3:3.5 in 50:50 DMSO:water, pH 6.5, and reacting overnight at 60° C. under mild stirring (Scheme 1, fourth row). The resulting 5FURW was purified via reverse phase chromatography using Sep-Pack C18 cartridges (Waters) and dried under vacuum.

(viii) Characterization of 5FU Analogues

Mass spectrometry and nuclear magnetic resonance (NMR) spectrometry were utilized to characterize 5FU analogues synthesized above. For mass spectrometry, samples were analyzed on a Waters QTOF2 tandem MS system is equipped with an electrospray ionization (ESI) source. For NMR, $^1$H spectra were collected on a Varian VNMRS 600 MHz spectrometer.

(ix) Drug Encapsulation into Liposomes

Drug encapsulation was evaluated for each drug, and the encapsulation methods reported here provided the highest yield for each respective drug. DOX, 5FU conjugated to tryptophan (5FUW), or 5FUR conjugated to tryptophan (5FURW) were incubated with liposomes after generation of the transmembrane ammonium sulfate gradient, for 30 minutes, 2 hours, or 2 hours, respectively, at 65° C. 5FU was incorporated in the organic phase, prior to the lipid film formation, due to its poor water solubility. 5FU conjugated to glycine (5FUG) or 5-fluorouridine (5FUR) was introduced in the ammonium sulfate film hydration solution upon vesicle formulation. For DOX and 5FURW co-loaded liposomes, 5FURW was first incubated with liposomes after generation of the transmembrane ammonium sulfate gradient for 2 hours, followed by DOX incubation for 30 minutes.

To remove free drug, liposomes were finally passed through a Sephadex G-25 PD-10 column.

Results (i) Chemotherapy Combination Studies—Evaluation of Drug Ratios

An important factor which governs the clinical applicability of chemotherapy combinations is the adverse side effects that occur when multiple drugs accumulate in healthy tissue rather than tumors. Because chemotherapy drugs cannot distinguish between healthy and malignant cells, they can easily distribute throughout the body, and toxicity is an inherent challenge. Although nanoparticles can promote drug accumulation in tumors via the EPR effect, it does not eliminate uptake in healthy tissue.

5FU+DOX are commonly incorporated in various combination chemotherapy regimens, but fundamental drug interaction studies between these drugs are lacking. To determine ratios of drugs which maximize cancer cell kill, 5FU+DOX were exposed to BT-474 human breast cancer cells at various ratios and evaluated for synergistic cell growth inhibition utilizing the Combination Index (CI) method (Chou and Talalay, Advances in enzyme regulation 1984, 22: 27-55). As seen in FIG. 2A, at a constant 5FU concentration, the ratio which yielded the lowest CI, and hence greatest synergy, was R=819:1±64 5FU:DOX. At R<819, the pair exhibited additivism (CI=1), and at R>819, the pair elicited antagonistic interactions with CI>1. Although R=819 synergistically inhibited cancer cell growth, the same was not true for MCF 10A epithelial control cells. This is represented by direct comparisons of $D_{50}$ concentrations for BT-474 and MCF 10A cells in a relative ratio, as seen in FIG. 2B. High $D_{50}$ ratios indicate higher drug concentrations required to kill cancer cells compared to epithelial cells, and vice versa. In this manner, direct comparisons of $D_{50}$ concentrations for cancer cells relative to healthy cells can act as a specificity, and hence toxicity, metric. As seen in FIG. 2B, the $D_{50}$ ratio for both 5FU and DOX was reduced by combining them in the synergistic ratio R=819, relative to individual drug administrations. The $D_{50}$ ratio was reduced by 36-fold and 5-fold for 5FU and DOX, respectively. This shows that the drugs are more toxic to healthy cells when used alone, but a synergistic combination of the drugs preferentially inhibits cancer cells.

Furthermore, the pair of drugs 5FU and DOX consistently outperformed cell inhibition of either individual drug when combined at R=819 (FIGS. 3A and 3B). On the contrary, 5FU+DOX at antagonistic ratio R=6551±170 consistently inhibited less cancer cell growth than 5FU treatment alone.

To assess potential toxic effects that may occur in vivo, 5FU+DOX was challenged in vitro against two representative healthy cell lines, bEnd.3 mouse brain endothelial cells and MCF 10A human breast epithelial cells. These cell types were chosen because any systemically-administered drug is susceptible to interactions and uptake by endothelial cells, as well as epithelial cells in surrounding healthy tissue. 5FU+DOX were exposed to each cell line in the synergistic and antagonistic ratios of R=819 and R=6551, respectively, and toxicity was assessed via MTT assays.

The combination toxicities were also compared to 5FU treatment alone and DOX treatment alone, and the results are shown in FIGS. 3C-4F. Cell inhibition studies in FIGS. 3C-3F verify that 5FU+DOX at both R=819 and R=6551 is less toxic than single drug treatments in endothelial and epithelial cell lines bEnd.3 and MCF 10A, respectively.

(ii) Effect of Cationic Charge on Liposomal DOX Activity

Both cellular uptake and intracellular payload release can be enhanced with cationic lipids (Zelphati, O. and F. C. Szoka, Proc. Natl. Acad. Sci. USA 1996, 93(21), 11493-8; Bennett, et al., Molecular Pharmacology 1992, 41(6), 1023-1033; Friend, et al., Biochimica et Biophysica Acta (BBA)—Biomembranes 1996, 1278(1), 41-50), and can promote subsequent drug interactions with intracellular targets. Since poor DOX release is an inherent issue when incorporated via the nearly irreversible transmembrane ammonium sulfate gradient, a small fraction of cationic lipids was embedded in the liposome membrane. Moreover, cationic liposomes preferentially accumulate in tumor endothelium compared to neutral and negatively-charged vesicles (Thurston, et al., The Journal of clinical investigation 1998, 101(7), 1401-13; Kalra and Campbell, Pharmaceutical research 2006, 23(12), 2809-17; Campbell, et al., Cancer Research 2002, 62, 6831-6836), and can provide tumor-honing properties complementary to the EPR effect. Properties of neutral (DOX-L) and cationic (+DOX-L) DOX-liposomes are provided in Table 1.

TABLE 1

Physical and chemical properties of DOX-loaded liposomes (N ≥ 3). Data expressed as mean ± SD (N = 3)

| Liposome Formulation | Liposome Composition | Size (nm) | Zeta Potential (mV) | Drug Incorporation (mol %) |
|---|---|---|---|---|
| DOX-L | 55:45 DSPC:Chol | 154.5 ± 5.0 | −9.55 ± 3.56 | ~1.08 ± 0.16 |
| +DOX-L | 80:10:10 DSPC:DOTAP:Chol | 155.6 ± 5.3 | 39.93 ± 4.81 | ~0.96 ± 0.13 |

Incorporation of 10 mol % DOTAP lipids shifted the ζ potential from −9.55 mV (zwitterionic liposomes) to +39.93 mV, without affecting liposome size or drug encapsulation. Drug activity (FIG. 4A), however, was significantly enhanced upon cationic lipid incorporation. The DOX-equivalent $D_{50}$ concentration was reduced 5-fold, from 33.5 µM to 6.7 between the zwitterionic and cationic liposomal formulations, respectively. Both DOX-L and +DOX-L were less active compared to free DOX ($D_{50}$=0.3 µM), which is expected since liposomes must first overcome the added barrier of active cell internalization before DOX can reach its intracellular target.

To comprehend the improvement in DOX activity in +DOX-L compared to DOX-L, drug internalization studies were conducted. BT-474 cells were incubated with free DOX, DOX-L or +DOX-L at drug-equivalent concentrations of 1 µM and subsequently imaged via confocal microscopy in order to visualize and quantify internalized DOX. Similar intracellular DOX concentrations were observed when cells were exposed to either free DOX or DOX-L. However, cells incubated with +DOX-L exhibited greater DOX fluorescence than those exposed to DOX or DOX-L. Quantification of averaged fluorescence intensities is provided in FIG. 4B, and indeed shows no statistical difference between DOX- and DOX-L-treated cells, but a 12-fold enhancement in DOX fluorescence of +DOX-L compared to DOX-L. These results elucidate that cationic lipids improve DOX uptake and intracellular concentration, and verify the use of positively-charged lipids to promote DOX release. All liposome formulations evaluated thereafter included 10% cationic lipids in order to facilitate drug release and to better preserve anticancer activity.

(iii) Drug Encapsulation into Liposomes
(a) Incorporation of 5FU in Liposomes

To maintain synergistic drug ratios in vivo, both drugs are preferably entrapped in the same vehicle so as to circulate systemically as one unit in the prescribed ratio. The transmembrane ammonium sulfate gradient, however, was developed specifically for incorporation of amphipathic anthracyclines, and presents difficulty for the entrapment of agents from different drug classes. Thus, to incorporate 5FU and DOX in the same liposome, various modifications of 5FU were introduced and investigated for compatibility with the transmembrane ammonium sulfate gradient. Table 2 summarizes the different 5FU analogues which were investigated utilizing the cationic formulation described above. Unmodified 5FU was only incorporated at 0.7 mol % relative to lipids, and substantiated the need for a different 5FU liposomal encapsulation method.

All 5FU analogues were designed to improve drug encapsulation in liposomes. The overarching concept of all analogues was to synthesize prodrugs of 5FU, wherein the cleavable component vested similar chemical properties as DOX, such as amphipathicity, aromaticity and weak basicity. The first attempt aimed to improve the basicity of 5FU through the incorporation of a free amine. The free amine in DOX governs its ability to form a salt in the presence of ammonium sulfate. To incorporate an inherently non-toxic free amine, the simplest amino acid, glycine, was conjugated to 5FU. 5FU conjugated to glycine (5FUG) was achieved by the reactions described in Scheme 1 and verified by mass spectrometry. 5FUG encapsulation yield in liposomes was 1.4 mol %, double that of unmodified 5FU (Table 2).

TABLE 2

Physical and chemical properties of liposomes containing 5FU analogues with lipid composition of 80:10:10 DSPC:DOTAP:Chol (N ≥ 3)

| 5FU Analogue | Drug Incorporation (mol %) | Size (nm) | Zeta Potential (mV) |
| --- | --- | --- | --- |
| 5FU | 0.7 ± 0.2 | 173.5 ± 43 | 41.7 ± 9.8 |
| 5FUG | 1.4 ± 0.5 | 161.8 ± 10.8 | 41.2 ± 1.8 |
| 5FUW | 3.2 ± 0.4 | 167.4 ± 1.8 | 19.6 ± 0.6 |
| 5FUR | 3.7 ± 0.2 | 177.4 ± 2.8 | 37.9 ± 1.0 |

TABLE 2-continued

Physical and chemical properties of liposomes containing 5FU analogues
with lipid composition of 80:10:10 DSPC:DOTAP:Chol (N ≥ 3)

| 5FU Analogue | Drug Incorporation (mol %) | Size (nm) | Zeta Potential (mV) |
|---|---|---|---|
| 5FURW | 26.6 ± 2.4 | 163.8 ± 17.2 | 32.2 ± 6.5 |

However, to be able to select ratios in liposomes co-loaded with DOX, 5FU encapsulation should be similar to that of DOX, ~14-24 mol % (Haran, et al., Biochimica et Biophysica Acta 1993, 1151(2), 201-15). 5FUG still yielded one order of magnitude lower encapsulation compared to DOX, despite the added free amine to improve drug basicity.

The next derivative investigated was tryptophan conjugated to 5FU (5FUW), utilizing the same chemistry as 5FUG. Tryptophan also bears a free amine, but contrary to glycine, is also aromatic due to its indole moiety. Aromaticity plays a significant role in liposomal DOX encapsulation, as the intra-liposomal oligomerization of DOX is attributed to the H electron stacking of planar aromatic rings (Barenholz, et al., Medicinal Research Reviews 1993, 13(4), 449-491). Integration of planar aromatic rings in a 5FU prodrug can facilitate H electron stacking to other 5FU prodrugs as well as to DOX, and can potentially improve retention of 5FU. Free amine and aromaticity additions in the 5FU analogue 5FUW slightly improved drug incorporation to 3.2 mol %, and additional 5FU analogues were further investigated to enhance encapsulation.

5-fluorouridine (5FUR) is the ribosylated nucleoside analogue of 5FU, and is both a metabolite and precursor of the original drug. 5FU can be converted to 5FUR and vice versa in vivo through uridine phosphorylase, and thus both 5FUR and 5FU are metabolized to the same active products, 5-fluorouridine monophosphate (FUMP) and 5-fluorodeoxyuridine monophosphate (FdUMP) to elicit both RNA and DNA damage, respectively (Longley and Johnston, 2007, Human Press Inc.: Totawa, N.J., p. 263-278; Longley, et al., Nature Reviews. Cancer 2003, 3(5), 330-8; Ishitsuka, et al., Gan., 1980, 71(1), 112-123). 5FUR was investigated for encapsulation in liposomes. 5FUR is commonly utilized as a plant growth regulator and is commercially available. As seen in Table 2, unmodified 5FUR can be incorporated in liposomes to a greater extent than 5FU, about a 5-fold enhancement to 3.7 mol % drug encapsulation. The more attractive advantage of utilizing 5FUR rather than 5FU, however, is that it inherently contains three hydroxyl groups for greater conjugation of amino acids.

The final derivate investigated for 5FU was 5FUR triply conjugated to tryptophan (5FURW) via hydroxyl groups. This modification further enhances basicity and aromaticity compared to 5FUG and 5FUW. Triple conjugation of tryptophan to 5FU was achieved through nucleophilic acyl substitution aided by EDC (Scheme 1), and was verified using nuclear magnetic resonance spectroscopy.

As seen in Table 2, 5FURW yielded the greatest entrapment of all 5FU analogues considered, a 38-fold enhancement to 26.6 mol %, which is very similar to DOX encapsulation yields. The methodology to synthesize a 5FU analogue similar to DOX in both basicity and aromaticity resulted in encapsulation yields identical to that of DOX. Therefore, 5FURW served as the 5FU analogue for further co-encapsulation with DOX in liposomes.

(b) Retaining Synergistic Activity of 5FURW and DOX

Retaining drug synergy, however, is of the utmost importance next to feasible encapsulations of both drugs. Prior to incorporating both 5FURW and DOX in liposomes, synergistic ratios between the new 5FU analogue and DOX were identified. BT-474 cells were exposed to various ratios of 5FURW+DOX, and synergistic interactions were assessed utilizing the CI method. Since 5FURW hydrolyzes directly to its precursor, 5FUR, synergistic interactions were also investigated between 5FUR+DOX. FIGS. 5A and 5B show that 5FURW exhibits the same anticancer activity as unmodified 5FUR.

The dependence of anticancer synergy on 5FUR+DOX or 5FURW+DOX ratio is seen in FIG. 6A. Slight synergy occurred when low doses of 5FURW were combined with high doses of DOX (R=0.1), and extreme synergy was observed when high doses of 5FURW were combined with low doses of DOX (R≥75). 5FUR and DOX exhibit synergy at extreme ratios (R≤1 and R=600), as well. These synergistic regimes are similar to the original synergistic interactions observed with unmodified 5FU and DOX, which occurred at R≤0.5 and R=819. While the exact synergistic ratios are slightly different for each 5FU analogue, the regimes of synergy are similar across the various analogues of 5FU tested, and attests to the potent interactions between this combination. Without being bound by theory, the discrepancies between exact ratios may be attributed to the need for hydrolytic cleavage or metabolization prior to the interactions of the active forms of both drugs. FIGS. 6B and 6C show that the hydrolyzable moiety, tryptophan, was non-toxic for 5FURW doses utilized in these studies; therefore, synergy is attributed to 5FUR+DOX interactions.

After verifying that 5FURW was both easily incorporated in liposomes and synergistic with DOX, single-drug loaded liposomes were tested for synergy to assess if particle encapsulation compromises drug synergy. CIs were calculated for 5FURW-L and +DOX-L exposed to BT-474 cells. The results are provided in FIG. 6D. Contrary to their free drug counterparts, single drug-loaded liposomes only synergistically inhibited cancer cell growth at one extreme regime, R≤1. Although free drugs were synergistic for R>75, liposome-encapsulated forms were highly antagonistic (C>>1), with CIs two orders of magnitude greater than those of the synergistic ratios. 5FU+DOX consistently elicited synergistic cancer cell kill at R≤1, regardless of delivery method.

(c) Co-Incorporation of 5FURW and DOX in Liposomes

Two ratios of 5FU+DOX, one synergistic and one antagonistic, were incorporated in liposomes, and a third formulation of PEGylated synergistic liposomes was fabricated for in vivo purposes. Physical and chemical properties of all three formulations are listed in Table 3.

TABLE 3

Physical and chemical properties of liposomes containing both 5FURW and DOX

| Liposome Formulation[a] | R (5FURW:DOX) | DOX Incorporation (mol %) | 5FURW Incorporation (mol %) | Size (nm) | Zeta Potential (mV) |
|---|---|---|---|---|---|
| antFD-L | 12.2 | 0.45 ± 0.02 | 5.47 ± 0.94 | 156.9 ± 5.7 | 36.2 ± 0.5 |
| synFD-L | 0.18 | 7.75 ± 0.09 | 1.41 ± 0.47 | 149.8 ± 15.1 | 35.7 ± 4.3 |
| synPFD-L | 0.15 | 14.82 ± 0.69 | 2.17 ± 0.23 | 168.8 ± 18.7 | −23.0 ± 3.0 |

[a]The lipid composition was 80:10:10 DSPC:DOTAP:Chol, except for synPFD-L, which was 75:5:10:10 DSPC:mPEG-DSPE:DOTAP:Chol. Drug loadings and DLS measurements are reported as mean ± SD (N ≥ 3).

Liposomes bearing R=12.2 were designated as antFD-L, as their free drug contents exhibited CI>1. Similarly, liposomes carrying R=0.18 were designated as synFD-L, as their free drug contents elicited CI<1. Sizes and diameters of antFD-L and synFD-L were very similar (156.9 nm vs. 149.8 nm and 36.2 mV vs. 35.7 mV, respectively); the primary difference between the two formulations was the ratio of their drug payloads. In FIG. 7A, antFD-L exhibits similar cancer cell growth inhibition as liposomes containing only 5FURW. On the contrary, synFD-L exhibits superior cell kill compared to either 5FURW- or DOX-loaded liposomes (FIGS. 7A and 7B). To quantitatively compare antFD-L and synFD-L, CIs were calculated and averaged for all concentrations tested. antFD-L elicited CI=1.92±1.21, indicating antagonistic cancer cell kill, and synFD-L resulted in CI-0.31±0.24, showing synergistic cell kill. Thus, drug interactions in co-loaded liposomes were consistent with free drug interactions found in FIG. 6A.

PEGylation of liposomes, especially positively charged, is necessary for prolonged systemic circulation in order to prevent opsonization (Levchenko and Rammohan, International Journal of Pharmaceutics 2002, 240, 95-102; Klibanov and Maruyama, Biochimica et Biophysica Acta (BBA) 1991, 1062, 142-148). Therefore, a PEGylated version of synFD-L was fabricated, synPFD-L. A small fraction (5 mol %) PEG2000-DSPE was incorporated in the lipid bilayer, and resulted in a slightly larger size of 168.8 nm compared to synFD-L (149.8 nm), as well as a change in potential. Upon PEGylation, the cationic lipids became shielded, as was evident in the ζ potential of −23.0 mV. Drug encapsulations and ratios were only slightly altered. The inclusion of PEG allowed twice as much DOX retention compared to non-shielded liposomes. Therefore, encapsulated R shifted from R=0.18 to R=0.15, in favor of greater free drug synergy. The anticancer activity of synPFD-L surpassed that of synFD-L, as seen in FIGS. 7A and 7B.

Drug release studies in FIG. 7C show that 5FURW is released slightly faster than DOX, and that acidic conditions accelerate drug release. Therefore, the effective free drug R exposed to cancer cells is slightly higher than the R encapsulated in liposomes, but is still potent at inhibiting cell growth.

Example 2. In Vivo Pharmacokinetics (i) In Vivo Tumor Growth Inhibition

To assess tumor growth inhibition in vivo, a 4T1 murine breast carcinoma model was adopted. Female BALB/c mice six to eight weeks in age (Charles River Laboratories) were injected subcutaneously with $1 \times 10^5$ 4 T1 cells in the abdominal mammary gland. In preparation for inoculation, 4T1 cells were washed twice in PBS and finally suspended in sterile saline (0.9 wt/vol. % NaCl). Post-inoculation, mice were randomized into experimental and control groups, and were monitored daily for tumor growth and weight changes. Mice were treated with i.v. tail injections of either synPFD-L or free 5FURW combined with free DOX, at drug-equivalent doses of 3 mg/kg DOX and 0.6 mg/kg 5FURW diluted in sterile saline. Treatments began on day 3 post tumor inoculation, and were repeated every other day for a total of 4 injections. Tumor volumes were calculated as V=½(l)×(w)², where l and w correspond to the longest and shortest tumor diameters, respectively, as measured by a digital caliper. Body weights were also measured daily to assess overall health. All experiments were performed according to approved protocols by the Institutional Animal Care and Use Committee of the University of California, Santa Barbara.

(ii) In Vivo Biodistribution

Biodistribution studies were conducted by embedding the nonexchangeable and nonmetabolizable lipid marker [$^3$H]-cholesteryl hexadecyl ether (CHDE; Perkin Elmer, Waltham, Mass.) (Pool, et al., Lipids 1982, 17(6), 448-452) in the liposome membrane. CHDE was dissolved at a ratio of 0.5 μCi/μmol phospholipid prior to thin film formation, and liposome fabrication proceeded as described above. BALB/c mice bearing 100 mm³ 4 T1 tumors were administered [$^3$H]-liposomes at drug equivalent doses of 6 mg/kg DOX+1.2 mg/kg 5FURW via i.v. tail vein injection, and were euthanized 6 hours post-injection. Solvable (Perkin Elmer, Waltham, Mass.), 5 mL, was added to harvested heart, lung, liver, spleen, kidney and tumor organs, and incubated overnight at 60° C. Ultima Gold (Perkin-Elmer), 10 mL, was added to organ solutions, and radioactive content was measured in a Packard TriCarb 2100TR scintillation counter. Results were reported as organ disintegrations per minute (DPM) relative to initial dose DPM, normalized to organ weight.

Results (i) In Vivo Tumor Growth Inhibition

The potent multi-drug loaded liposomes were challenged in vivo against a highly metastatic and aggressive 4T1 mouse breast cancer model to assess their ability to maintain synergistic drug activity when faced with advanced, difficult to treat cancers. This model was also chosen for its robust tumor formation in immuno-competent BALB/c mice, which allows for a more accurate depiction of nanoparticle clearance and efficacy compared to models in immuno-incompetent mice. PEGylated liposomes, synPFD-L, were challenged against 4T1 murine breast carcinoma in vivo, at drug-equivalent doses of 3 mg/kg DOX+0.62 mg/kg 5FURW for a total of 4 alternating i.v. injections starting on Day 3. As seen in FIG. 8A, significant tumor reduction was achieved by synPFD-L. By day 23, the last day of >50% untreated mice survival, liposomes elicited 91% (77 vs. 904 mm$^3$) tumor growth inhibition, whereas free 5FURW+DOX at the same doses were only capable of inhibiting 39% tumor growth (547 vs. 904 mm$^3$). Moreover, all tumors treated with free 5FURW+DOX eventually grew to the same sizes as control mice, and hence were only able to extend average survival of untreated mice by 4 days (24 vs. 28 days), FIGS. 8A and 8C. Daily monitoring of body weights (FIG. 8B) also showed that the both synPFD-L and free 5FURW+DOX were well-tolerated, as no significant reductions in body weight were observed. The fractional change in body weight was not statistically different across control and experimental groups for the duration of the experiments.

To show the therapeutic efficacy of co-loaded liposomes, individual tumor growth profiles for each mouse treated with synPFD-L are provided in FIG. 8D. Contrary to free drug-treated mice, most liposome-treated mice reached a peak tumor volume between 50-80 mm$^3$ on Day 28, followed by tumor regression and finally, complete eradication. Only 3 of 8 tumors from this group eventually grew normally. No detectable tumors in 5 of 8 mice were observed for the remainder of the study. Therefore, the average survival of untreated mice was significantly extended by at least 30 days when treated with the synergistic synPFD-L. As shown herein, 4T1 tumor growth was inhibited by >90% at a cumulative DOX dose<15 mg/kg. This was not previously accomplished, either when used as a single agent or combined with another chemotherapy drug (Sun, et al., Biomaterials 2013, 34(28), 6818-28; Charrois, et al., Journal of Pharmacology and Experimental Therapeutics 2003, 306(3), 1058-1067; Liu, et al., Molecular Pharmaceutics 2014, 11, 1651-1661; Du, et al., Cancer Chemotherapy and Pharmacology 2010, 65(2), 277-287; Bandyopadhyay, et al., PLOS ONE 2010, 5(4), e10365-e10365; Wang, et al., International Journal of Oncology 2007, 30(4), 947-953; Wang, et al., Biomaterials 2012, 33(28), 6877-6888; Liu, et al., Oncology Reports 2012, 27(3), 678-684; Mastria, et al., Journal of Controlled Release 2015, 208, 52-58).

(ii) In Vivo Biodistribution Studies

In vivo biodistribution studies were conducted to see if therapeutic effect was dictated by high uptake in tumors (FIG. 8E). However, synPFD-L exhibited biodistributions typical of PEGylated liposomes (Liu, et al., Molecular Pharmaceutics 2014, 11, 1651-1661; Chang, et al., Anticancer Research 2007, 27(4B), 2217-2225; Harrington, et al., British Journal of Cancer 2000, 83(2), 232), with greatest accumulation occurring in the liver and spleen, and 2.3% initial dose per g (ID/g) present in tumors. Therefore, the enhanced therapeutic efficacy is likely attributed to the potent synergistic interactions between 5FURW+DOX.

Example 3. Mechanistic Study of 5FU and DOX Synergy Via the Generation of Reactive Oxygen Species (ROS)

Materials and Methods

Reactive Oxygen Species Studies

To understand the cause of synergistic interactions between 5FU and DOX, one of the mechanisms DOX utilizes to induce cell death was investigated: reactive oxygen species (ROS) generation. DOX is known to induce apoptosis in endothelial and tumor cells by different mechanisms. In endothelial cells, DOX induces cell death by ROS generation, whereas in tumor cells, DOX induces apoptosis by activating the p53 tumor suppressor gene (Wang, et al., The Journal of Biological Chemistry 2004, 279(24), 25535-43). By comparing ROS generation in cancer cells exposed to 5FU and DOX rather than DOX alone, one can investigate the impact of 5FU on DOX cancer cell cytotoxicity.

To visualize and assess the production of reactive oxygen species (ROS), cells were seeded in an 8-well chambered borosilicate coverglass (Nunc Lab-Tek) at a density of 85,000 cells per well in 300 µL medium and grown overnight prior to incubation with drug solutions in fresh medium. After incubation of BT-474 cells with either 5FU and DOX at a molar ratio of 819:1, 5FU alone, or DOX alone for 72 hours, cells were washed three times in PBS and exposed to 10 µM carboxy-H$_2$DCFDA (Invitrogen Life Technologies) in phosphate buffered saline (PBS; Theimo Scientific) for 30 minutes at 37° C. and 5% CO$_2$. Upon acetate cleavage and oxidation, carboxy-H$_2$DCFDA formed carboxydichlorofluorescein and acted as an ROS indicator. Cells were washed thrice more in PBS, finally suspended in cell culture medium, and immediately imaged live using an Olympus Fluoview 1000 spectral confocal microscope. Carboxydichlorofluorescein and DOX were both excited utilizing a 488 nm 10 mW Argon gas laser and visualized with 492-560 nm and 574-674 nm optical filters, respectively. Images were captured as 10 µm z-stacks, and each z-stack was averaged into a single image using ImageJ 1.47 h software (NIH). Fluorescence intensity is reported as the raw integrated density divided by number of cells, determined by DOX fluorescence which coincided with cell nuclei.

Results

Figure 9:
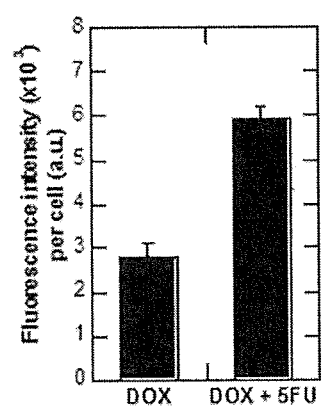
FIG. 9. Carboxy-$H_2$DCFDA fluorescence intensity is reported as mean±SD (N=3). Representative images are shown as an average of 10 µm z-stacks. Scale bar=20 µm. **, P<0.01 performed by two-tailed Student's t-test.

Visualization of the incubated cells using confocal microscopy demonstrated that negligible ROS generation was present in untreated cells and cells incubated with 5FU alone. Little ROS generation was visualized in cells incubated with just DOX; on the contrary, significantly more ROS was present in cells treated with the combination of 5FU and DOX in a ratio of 819:1. Quantification of the ROS fluorescence indicator (FIG. 9) shows that ROS generation is slightly more than doubled when 5FU is included in the treatment compared to DOX incubated alone. Therefore, the addition of 5FU amplifies the non-traditional mechanism by which DOX induces apoptosis in cancer cells.

Overall, the data shown in the examples above demonstrate that low dose chemotherapy, if co-delivered in synergistic ratios, is in fact capable of completely regressing tumors. Chemotherapy efficacy is hindered by poor specificity, and distribution to healthy organs renders nanoparticle delivery imperative, which promotes accumulation in tumors via the EPR effect.

Ratios have long been determined to dictate combination chemotherapy potency in vitro, but FDA-approved combinations have yet to incorporate this important factor. The Examples provided herein show the ramifications ratio can impose on both anticancer activity and off-target toxicity. The most effective synergistic ratio for 5FU+DOX was R=819:1±64 5FU:DOX, with CI=0.34±0.12. At this ratio, 86% of BT-474 cancer cell growth was inhibited at 5FU concentrations which normally only inhibit 40% cell growth, FIG. 3B. However, the same drug pair at R=6551±170 antagonistically inhibited cancer cell growth. At this ratio, all investigated 5FU+DOX concentrations were actually less active at killing cancer cells compared to 5FU alone, FIG. 3B.

Studies with healthy breast epithelial cell line MCF 10A also introduced another advantage of ratiometric delivery: selective cancer cell toxicity. As seen in FIG. 2B, relative $D_{50}$ concentrations for BT-474 and MCF 10A were significantly reduced when incubated with cells at a synergistic drug ratio of R=819 compared to free drug treatment. This shows that at synergistic R, much less total drug dose is required to kill cancer cells compared to MCF 10A. The reverse was also true; at antagonistic R or even free drug incubations, less drug is required to inhibit healthy MCF 10A cell growth compared to malignant cells. A similar trend was observed for a control endothelial cell line, bEnd.3, see FIG. 3C.

Results from these studies show that the enhanced cell inhibition of 5FU+DOX at R=819 is specific for cancer cells, and is not as toxic to endothelial or epithelial cells. In fact, the combination may not be any more toxic than either 5FU or DOX when administered as a single agent, because the combination, at best, only inhibits as much cell growth as DOX alone. This finding demonstrates that the combination of two cancer agents, as described herein can avoid a typical drawback associated with combination chemotherapies, i.e. amplified adverse side effects due to co-localization of multiple drugs in essential organs.

Figures 10A, 10B:
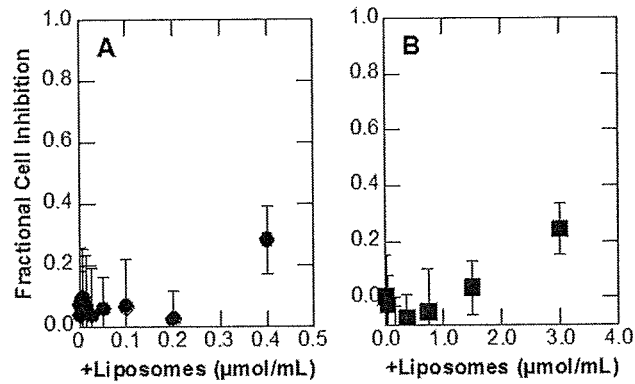
FIGS. 10A and 10B.

To incorporate a synergistic ratio of 5FU+DOX in a single, effective nanoparticle, a liposome formulation and 5FU entrapment methods were developed. As seen in FIG. 4A, a small fraction of cationic lipids (10 mol %) enhanced DOX delivery and activity relative to completely zwitterionic liposomes. This fraction was non-toxic at relevant concentrations for drug delivery (FIGS. 10A and 10B).

Co-incorporation of 5FU+DOX in liposomes also required the development of a high 5FU entrapment method compatible with the DOX transmembrane ammonium sulfate gradient. Various prodrug analogues were synthesized to bear hydrolyzable moieties that render it chemically similar to DOX. The prodrug, 5FURW, contained three ester-linked tryptophans to the ribosylated nucleoside analogue of 5FU, 5FUR. 5FURW is both basic due to the presence of multiple free amines, and capable of H stacking due to tryptophan's aromatic indole ring. 5FURW was incorporated in liposomes to the same extent as DOX (~26 mol % relative to lipids).

Previously, regardless of initial drug loading, time of drug and liposome contact, and temperature, 5FU was demonstrated to be incapable of measurable integration in liposomes with an acidic core (Costa and Moraes, Acta Sci Technol, 2003(1), 53-61). It was even previously reported that the exact opposite approach, utilizing basic media (~pH 8.6), is required for liposomal encapsulation of 5FU (Kaiser, et al., International Journal of Pharmaceutics 2003, 256(1-2), 123-131). 5FU has only been reported to exist in anionic forms, which occur at neutral pH (Markova and Ivanova, The Journal of Physical Chemistry A 2010, 114(50), 13154-62), and hence not in liposomes bearing an acidic pH gradient.

Thus, for the purpose of simultaneously co-delivering 5FU+DOX, a different method was developed. Free amine and aromatic modifications to 5FUR helped overcome the previously reported poor encapsulation issues, and were also designed to be hydrolyzable in order restore the active drug which is synergistic with DOX. One of skill in the art understands that this approach is applicable to the entire class of nucleobase analogue chemotherapies, such as cytarabine, gemcitabine, and decitabine, all of which contain pendant hydroxyl groups that can be conjugated to tryptophan or any other molecule of interest.

The tryptophan modifications to 5FUR did not compromise synergy with DOX. As seen in FIGS. 2A and 6A, 5FU+DOX, 5FUR+DOX and 5FURW+DOX all exhibited CI<1 and hence synergistic cancer cell kill at two regimes: R≤1 or R≥600. Synergy was altered when incorporated in liposomes, as 5FURW-L and +DOX-L were only synergistic at the former regime (FIG. 6B). At R=600, single drug-loaded liposomes exhibited CI=11.5±9.6, indicating antagonistic interactions, whereas free drugs exhibited synergy (CI=0.45±0.06). This ratio requires two orders greater magnitude concentration of 5FURW than DOX.

Liposomes reduce the amount of free DOX available to the cells, since added barriers of particle internalization, drug release, and precipitate dissolution are required to access free DOX. This is depicted in FIG. 4A, where free DOX outperformed cancer cell inhibition of either liposome formulation. Release studies in FIG. 7C also show that DOX releases from liposomes at a slower rate than 5FURW. Because of this reduced accessible DOX, the effective free R ratio may be much larger when 5FURW and DOX are administered in liposomes, and may negate expected synergistic interactions. Therefore, the synergistic regime of R≤1, rather than R≥600, was investigated for co-encapsulation of 5FURW and DOX in liposomes.

Similar to mixed single-drug loaded liposomes, 5FURW and DOX co-encapsulated in the same liposome at R≤1 inhibited greater cancer cell growth than either single-drug loaded liposome (FIGS. 7A-7C). This was evident for both non-PEGylated and PEGylated liposomes. However, the true merit of PEGylated 5FURW+DOX co-encapsulated liposomes was captured in vivo when challenged against a 4T1 murine mammary carcinoma model. Non-PEGylated synFD-L was unable to prolong survival rates, while PEGylated synPFD-L was able to completely reverse tumor growth and eradicate tumors in 62.5% of treated mice (FIGS. 8A and 8D).

It was observed that the low doses that were utilized were able to achieve significant therapeutic effects. Mice were treated with 4 total injections of 3 mg/kg DOX and 0.62 mg/kg 5FURW, for a total DOX and 5FURW dose of 12 mg/kg and 2.5 mg/kg, respectively. In prior studies, cumulative DOX doses<15 mg/kg have not been able to inhibit aggressive 4T1 tumor growth by >90%, regardless of its use as a single agent or in combination with another chemotherapy drug (Sun, et al., Biomaterials 2013, 34(28), 6818-28; Charrois and Allen, Journal of Pharmacology and Experimental Therapeutics 2003, 306(3), 1058-1067; Liu, et al., Molecular pharmaceutics 2014, 11, 1651-1661; Du, et al., Cancer Chemotherapy and Pharmacology 2010, 65(2), 277-287; Bandyopadhyay, et al., PLOS ONE 2010, 5(4), e10365-e10365; Wang, et al., International Journal of Oncology 2007, 30(4), 947-953; Wang, et al., Biomaterials 2012, 33(28), 6877-6888; Liu, et al., Oncology Reports 2012, 27(3), 678-684; Mastria, et al., Journal of Controlled Release 2015, 208, 52-58). Moreover, tumor eradication was maintained for the remainder of the study, and resulted in median survival rates greater than 60 days post-treatment.

These studies demonstrate that co-delivery in liposomes or nanoparticles is able to manifest the potency of 5FU+DOX in vivo; in contrast free drug equivalents were only able to prolong median survival rates from 24 to 28 days and were largely ineffective. Without being bound by theory, this is may be due to uncoordinated drug pharmacokinetics and fast plasma clearance of the small molecule drugs when injected intravenously (i.v.) as free solutions. Clinical studies have shown that 5FU and DOX exhibit elimination half-lives of 8-22 minutes (Diasio and Harris, Clinical Pharmacokinetics 1989, 16(4), 215-37) and 4-5 minutes (Gabizon, et al., Cancer Research 1994, 54, 987-992), respectively. Liposomes bearing synergistic ratios of chemotherapy drugs are being developed by Celator Pharmaceuticals for clinical use. One formulation is CPX-351, incorporating a synergistic ratio of 5:1 cytarabine:daunorubicin, which was shown to improve overall response rates compared to free drug equivalents in patients diagnosed with acute myeloid leukemia (Lancet, et al., Blood 2014, 123 (21), 3239-3246). In comparison to the studies described herein, however, cumulative chemotherapy doses>50 mg/kg were required to achieve long-term survival in a murine leukemia model (Mayer, et al., Molecular Cancer Therapeutics 2006, 5(7), 1854-63). Despite synergistic ratio conservation in liposomes, high chemotherapy doses were necessary to capture the pair's therapeutic potential in vivo.

This is contrary to the data provided herein, which involved <15 mg/kg cumulative chemotherapy doses for similar therapeutic effects.

Different lipids were used in CPX-351 compared to the formulations described herein. CPX-351 contains DSPC, distearoylphosphatidylglycerol (DSPG), and cholesterol, thereby only including zwitterionic and negatively-charged lipids.

In further contrast to the formulations described here, CPX-351 also lacks PEG for prolonged liposome circulation.

Example 4. Alternative Synthetic Strategy for 5FURW, Encapsulation, and In Vitro Pharmacokinetics An alternative synthetic strategy was developed for the synthesis of 5FURW. N-carboxy anhydride of tryptophan was selected as a non-limiting example. The presence of the N-carboxy anhydride group eliminates the requirement for an activating reagent. The nitrogen atom in the N-carboxy anhydride is protected with a Boc group that is easily removed with acid treatment. The BOC group forms a carbamate N-carboxy anhydride that is not polymerizable upon the opening of the N-carboxy anhydride ring by a nucleophile.

As described below, using this strategy, the intermediate and the final products were obtained in good yield, and each was characterized by NMR, mass spectroscopy, and UV-Vis.

(i) Synthesis of 5FURBocW—the Intermediate Product

5FUrd (48.50 mg, 184.98 μmol, Alfa Aesar J62083), Boc-Trp-N-carboxyanhydride (274.98 mg, 832.40 μmol, Santa Cruz Biotechnology sc-300294) and DMAP (6.78 mg, 55.49 μmol, Sigma Aldrich 107700) was solved in 10 mL of anhydrous DMF (Sigma Aldrich 227056) and allowed to react overnight at room temperature under inert atmosphere (Scheme 2).

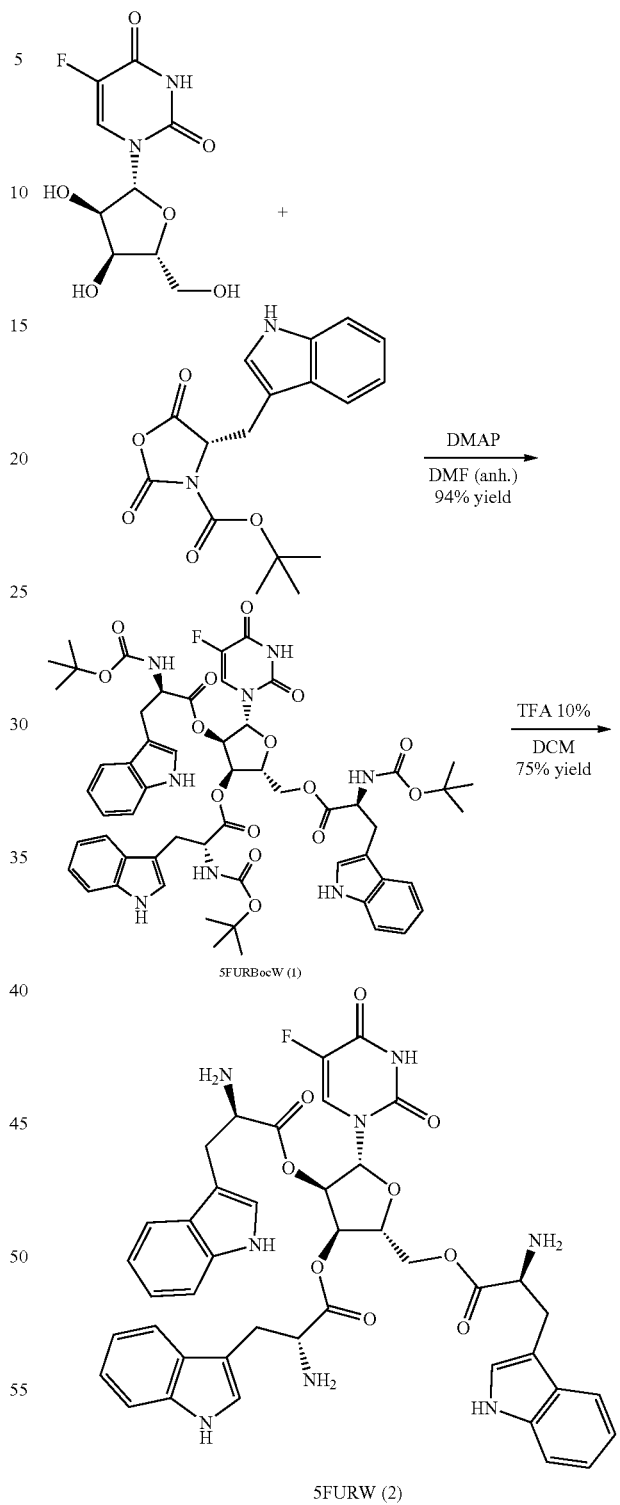

The mixture was evaporated until dryness and resulting oil was extracted with a mixture of HCl 1N and Ethyl acetate 1:1. The organic layer was separated, dried with MgSO$_4$, filtered and finally evaporated. Liquid obtained was purified by chromatography column (50 mg silica gel 60, 230-400 mesh, column dimensions d=3 cm) with dichloromethane and ethyl acetate (starting gradient dichloromethane:ethyl acetate 9:1, increasing to 1:1) to finally obtain a yellow liquid (194.4 mg, 94% yield). UV-Vis (MeOH): 270 nm. TLC (dichloromethane:ethyl acetate 5:95) Rf 0.71. $^1$H NMR (600 MHz, DMSO-d6) δ 11.96 (s, 1H, 116), 10.80 (s, 3H, H25 H39 H53), 8.21-7.92 (m, 1H, H2), 7.62-6.65 (m, 15H, tryptophan aromatic protons), 5.96 (d, J=5.4 Hz, 1H, H16), 5.73 (m, 1H, H11), 5.56 (m, 1H, H15), 5.35 (m, 1H, H13), 4.37-4.07 (m, 6H, H21 H35 H49), 3.21-2.85 (m, 6H, H22 H36 H50), 1.46-1.16 (m, 21H, tBu protons). MALDI-TOF: m/z calculated for $C_{57}H_{65}FN_8NaO_{15}^+$ [M+Na]$^+$ 1143.44, found 1143.20.

(ii) Synthesis of 5FURW—the Final Product

FURBocW (78.9 mg, 70.4 μmop were solved in 3 mL of dichloromethane and 200 μL of TFA were added to achieve a concentration of 10% of TFA. After half an hour solvent was evaporated until dryness. Product was redissolved in ethyl acetate and precipitated with dichloromethane. Finally, the desired product was obtained by filtration and washed with dichloromethane. A white powder (43.1 mg, 75% yield) was obtained. UV-Vis: 270 nm. TLC (dichloromethane:ethyl acetate 5:95) Rf 0.00. $^1$H NMR (600 MHz, DMSO-d$_6$) δ 12.10 (s, 1H, H6), 11.10 (m, 3H, H25 H39 H53), 8.80-8.33 (m, 6H, H2O H34 H48), 8.11 (d, J=6.8 Hz, 1H, H2), 7.65-6.83 (m, 15H, aromatic tryptophan protons), 5.93 (d, J=5.2 Hz, 1H, H11), 5.80-5.69 (m, 1H, H13), 5.50 (m, 2H, H15 H16), 4.47-4.19 (m, 5H, H17 H21 H35 H49), 3.54-3.10 (m, 6H, H22 H36 H50). MALDI-TOF: m/z calculated for $C_{42}H_{42}FN_8O_9^+$ [M+H]' 821.31, found 821.11.

(iii) Encapsulation of 5FURW

Figure 11A:
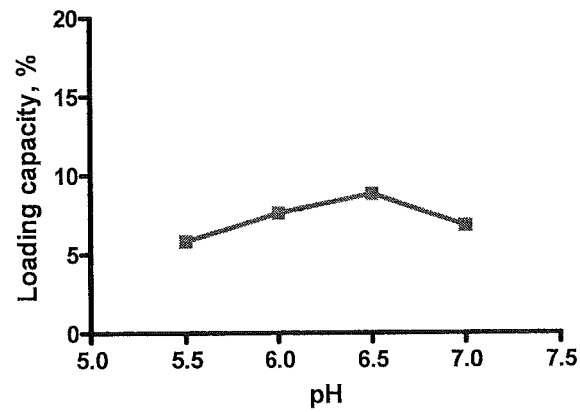
FIGS. 11A-11C. Dependence of the loading of 5FURW into liposomes on other parameters.
Figure 11B:
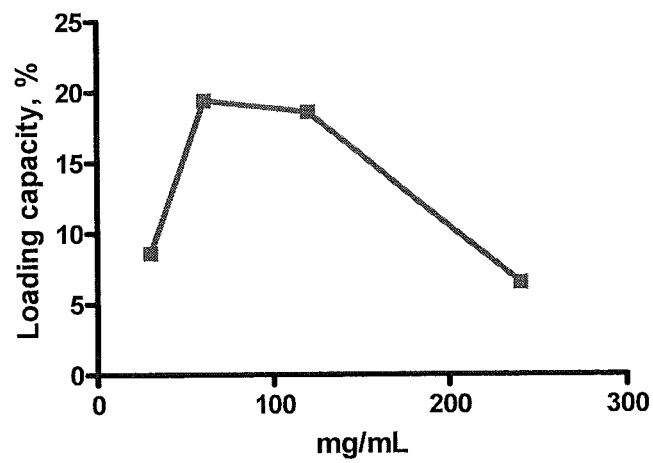
Figure 11C:
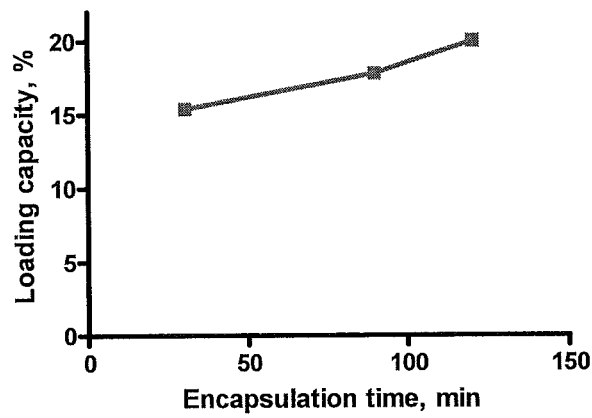
Figure 12A:
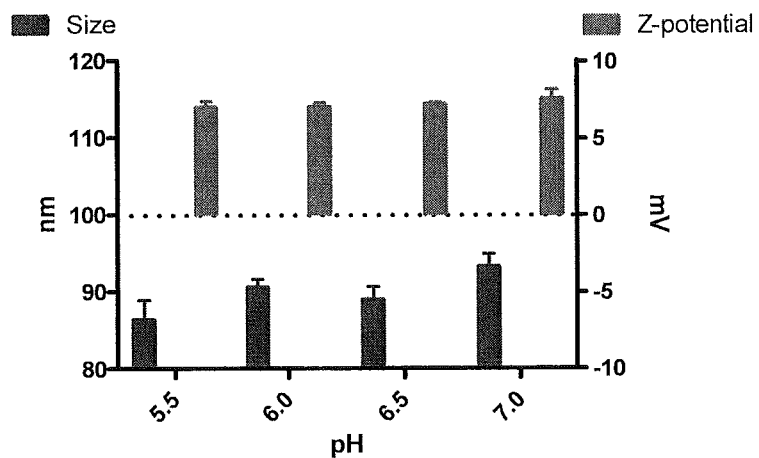
FIGS. 12A-12C. Dependence of the size and zeta-potential of 5FURW-loaded liposomes on other parameters.
Figure 12B:
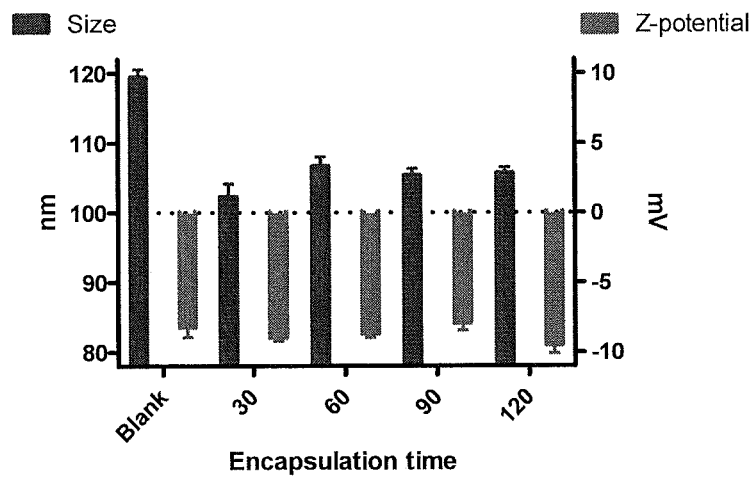
Figure 12C:
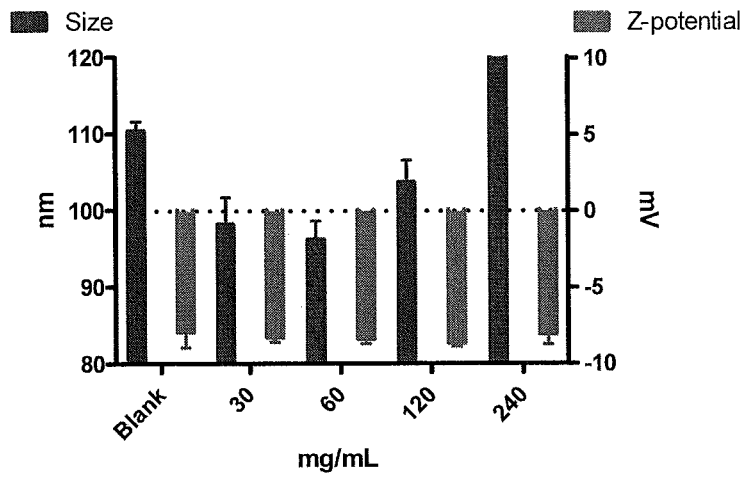

The procedure for encapsulation was based on a transmembrane ammonium sulfate gradient for the entrapment of amphipathic weak bases that provides a strategy for coencapsulation of other anticancer drugs as described above. Loading of 5FURW under several pH gradients was tested. The best encapsulation yield was obtained with an external pH of 6.5 (FIG. 11A). At this pH, the drug is completely soluble and also keeps a pH gradient with the inner buffer of the liposomes. Then the quantity of added drug was increased to raise the loading capacity, observing a saturation peak at 60 mg/mL and aggregation of liposomes at higher concentration of drug (FIG. 11B). Finally, encapsulation time was tested reporting a 20% of loading capacity after 2 h (FIG. 11C). Dependence of 5FURW liposomes on other parameters such as pH, encapsulation time, and drug concentration is shown in FIGS. 12A, 12B, and 12C, respectively. It should be noted that dynamic light scattering indicated the formation of aggregates. For instance, aggregation was observed in the 240-min time frame.

Liposomes were prepared with a mixture of DSPC:DSPE-PEG(2000)Amine or DSPE-PEG(2000)Carboxyl:Cholesterol:DOTAP with the ratio 75:5:10:10 via the thin lipid film formation. After the formation of the lipids and passing them through an extruder to obtain monodisperse 100 nm liposomes, the external solvent was changed using a size exclusion column and the drug encapsulated during two hours. Briefly, the thin lipid films were hydrated with 250 mM $(NH_4)SO_4$ to form liposomes containing either amine-terminated PEG or carboxy-terminated PEG. 1 mL of liposomes and 200 μL of 73 mM 5FURW were used for the encapsulation of 5FURW into the liposomes. The liposomes and 5FURW were incubated in a medium of 10 mM PBS at a pH of 6.5, at 65° C. for 2 hours for encapsulation to occur.

The encapsulation efficiency and loading capacity were calculated as follows:

$$\text{Encapsulation Efficiency } (EE, \%) = \frac{[5FURW_{final}]}{[5FURW_{initial}]}$$

$$\text{Loading capacity } (LC, \%) = \frac{[5FURW_{final}]}{[5FURW_{initial}]}$$

The liposomes were characterized using (i) the Steward assay to determine lipid concentration, (ii) absorbance at 270 nm to evaluate 5FURW concentration, and (iii) dynamic light scattering measurements to evaluate size and surface potential. The encapsulation efficiency and the loading capacity reported a 20% yield.

(iv) 5FURW Cell Studies

Figure 13A:
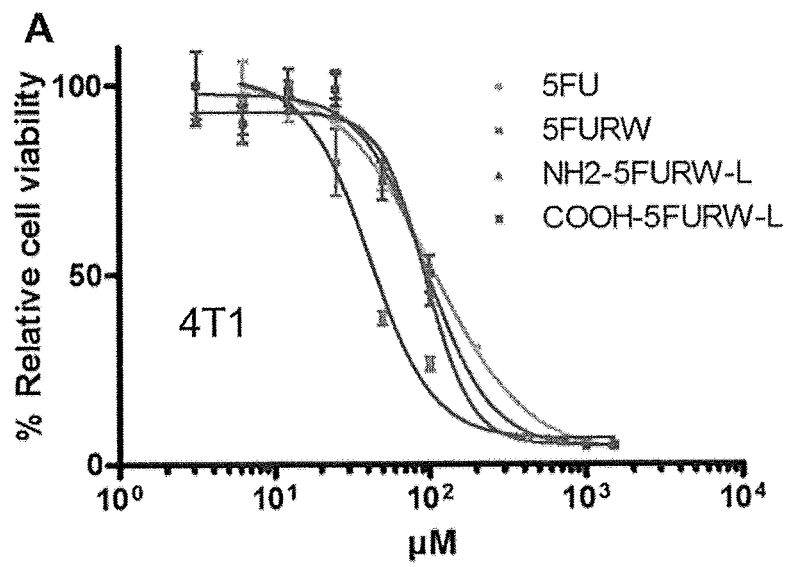
FIGS. 13A and 13B. Cell viability studies of two cancer cell lines unencapsulated 5FU, unencapsulated 5FURW, and 5FURW encapsulated in liposomes.
Figure 13B:
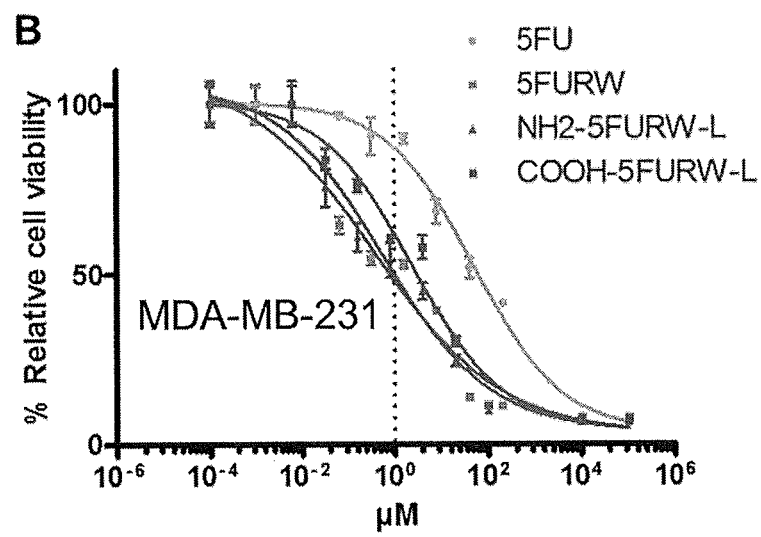

Two breast cancer cell lines (of mouse and human, 4T1 and MDA-MB-231) were tested with the synthesized 5FURW, compared with 5FU and also with encapsulated drug in liposomes functionalized with amino and carboxyl groups (Table 4, FIG. 13).

TABLE 4

Cell viability studies of two cancer cell lines using unencapsulated 5FU, unencapsulated 5FURW, and 5FURW encapsulated in liposomes.

| Composition | IC50 (μM) | |
|---|---|---|
| | 4T1 | MDA-MB-231 |
| 5FU | 104.2 | 50.44 |
| 5FURW | 41.25 | 0.3964 |
| 5FURW-L-NH2[a] | 95.17 | 0.6012 |
| 5FURW-L-COOH[b] | 95.66 | 2.409 |

5FURW encapsulated in liposomes containing
[a]amine-terminated PEG, and
[b]carboxy-terminated PEG.

For the breast cancer cell line 4T1, 5FURW was 2.5-fold more active than 5FU; for breast cancer cell line MDA-MB-231 5FURW was 127-fold higher. After encapsulating 5FURW in liposomes, its efficacy for MDA-MB-231 is 1.5 and 6-fold less than 5FURW, but for 4T1 cell line it was just 2-fold less (FIG. 13).

(v) In Vitro Synergy of 5FURW and DOX

Figure 14A:
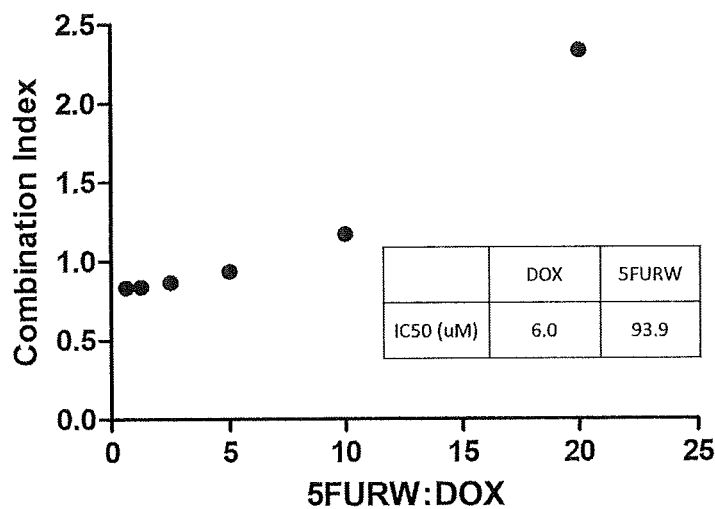
FIGS. 14A and 14B. Synergy of 5FURW and DOX in 4T1 cells.
Figure 14B:
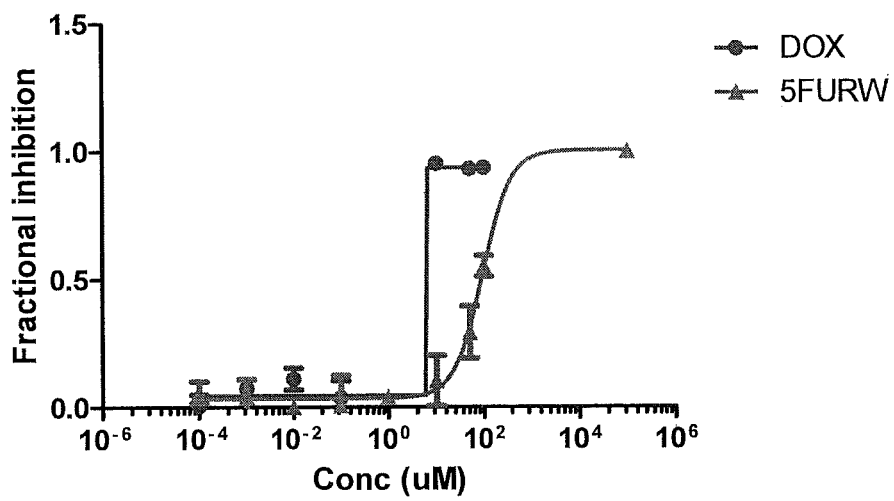

Combinations of 5FURW and DOX were tested in 4T1 cells for synergy (FIG. 14A). Varying concentrations of 5FURW were added to 5 uM of DOX to produce combinations ranging from 100 to 0.625 molar ratio of 5FURW:DOX. These combinations were given to 4T1 cells and incubated for 72 hours until assessment by MTT assay. The combination index (CI) was calculated as described by Chou (Chou, T. C., Pharmacol Rev, 2006. 58(3): p. 621-81). As a CI less than one indicates synergism, the results suggest that a ratio of less than five 5FURW:DOX is synergistic. The IC50 graphs used to complete the CI calculation and their corresponding IC50 values are displayed in FIG. 14B.

(vi) DAFODIL (5FURW AND DOX) Loading

Figure 15A:
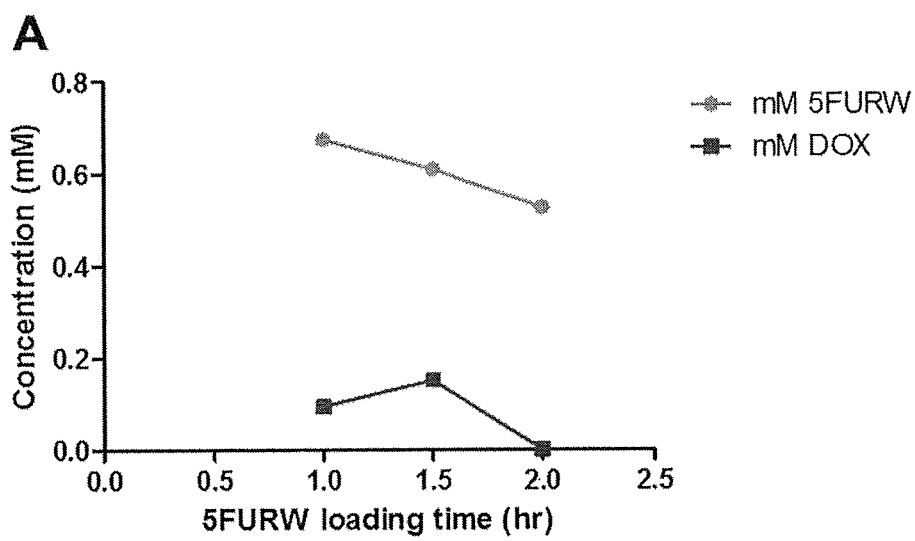
FIGS. 15A and 15B. Loading of DAFODIL (5FURW and DOX) into liposomes.
Figure 15B:
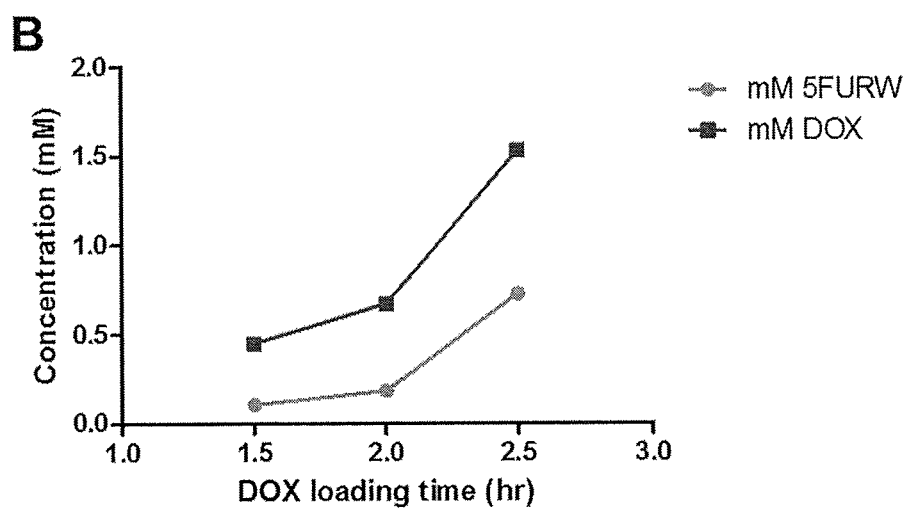

To encapsulate the drugs, 70 mM of 5FURW was added to the liposomes. After varying amounts of time, 70 mM of DOX was also added to the liposomes and allowed to equilibrate for 30 mins (FIG. 15A). However, under these conditions DOX was unable to load at a sufficient molar amount compared to the lipids, resulting in low loading capacities (LC %). Next, 70 mM DOX was added first to the liposomes first. After a varying amount of time, 5FURW was added and allowed to equilibrate for 1 hr (FIG. 15B). It was evident that not only did loaded DOX concentration increase with encapsulation time, but it was also being loaded with comparable LC % to the 5FURW, Table 5. DAFODIL was made with 18.49 LC % DOX and 23.09 LC % 5FURW, with encapsulation efficiencies of 34.48% and 23.63% respectively. The molar ratio of FURW:DOX is 1.25, determined using the LC % in Table 5. Particle size was shown to be stable through dynamic light scattering measurements. The average particle diameter was 101.9±0.82 nm.

TABLE 5

Characterization of drug-loaded liposomes

| | DOX | | | 5FURW | | |
|---|---|---|---|---|---|---|
| | Conc (mM) | EE % | LC % | Conc (mM) | EE % | LC % |
| DOX-L | 1.39 | 25.51 | 32.57 | — | | — |
| DAFODIL[a] | 1.76 | 34.48 | 18.49 | 2.20 | 23.63 | 23.09 |

[a]DOX-5FURW-L, i.e., liposome encapsulating DOX and 5FURW

The DAFODIL fabrication procedure was performed as follows. First, liposomes were formed through thin film hydration with a pH 5.5 of 250 mM ammonium sulfate buffer. Extrusion through a 100 nm polycarbonate membrane produces 100 nm liposomes, and size exclusion chromatography run with PBS pH 7.4 establishes the ammonium sulfate gradient across the liposome membrane. 50 µL of 70 mM DOX was added dropwise to 500 µL of liposomes under constant stirring at 65° C. and was left to equilibrate for two and a half hours in 10 mM PBS at pH 7.4. Next, 50 µL of 70 mM 5FURW was added under the same conditions and left to equilibrate for an additional hour. Finally, the drug-loaded liposomes were separated from the free drugs via size exclusion chromatography (PBS pH 7.4). Characterization consisted of absorbance measurements at 270 nm and 480 nm to determine the concentration of 5FURW and DOX, respectively, dynamic light scattering measurements to measure liposome size and surface potential, and Stewart assay to quantify the concentration of lipids in the sample.

Collectively, the Examples provided herein demonstrate the effectiveness of low dose chemotherapy, i.e. doses which were previously regarded as therapeutically inactive. By identifying and co-encapsulating synergistic chemotherapy combinations in liposomes, effective therapies can be delivered that are also safe.

We claim:

1. A pharmaceutical composition comprising a cationic liposome encapsulating 5FURW, wherein 5FURW has the structure

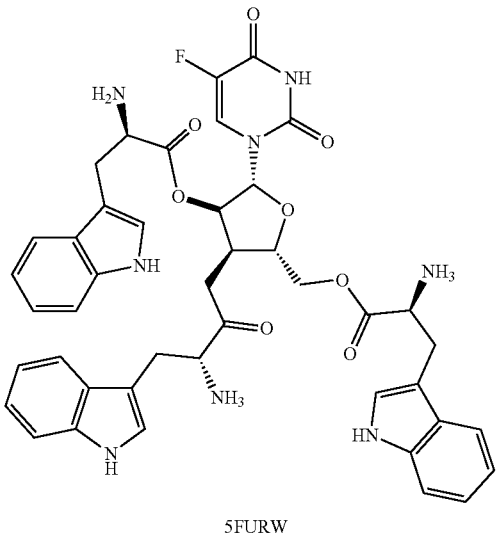

5FURW

2. The pharmaceutical composition of claim 1, further comprising an anthracycline.

3. The pharmaceutical composition of claim 2, wherein the anthracycline is doxorubicin.

4. The pharmaceutical composition of claim 1, wherein the liposome comprises cationic lipids and additionally comprises at least one lipid selected from the group consisting of zwitterionic lipids, PEGylated lipids, and combinations thereof.

5. The pharmaceutical composition of claim 4, wherein the liposome comprises a combination of cationic lipids, zwitterionic lipids, PEGylated lipids and cholesterol.

6. The pharmaceutical composition of claim 5, wherein the cationic lipids comprise 1,2-dioleoyl-3-trimethylammonium-propane (DOTAP), the zwitterionic lipids comprise 1,2-Distearoyl-sn-glycero-3-phosphocholine (DSPC), and the PEGylated lipids comprise 1,2-dioleoyl-sn-glycero-3-phosphoethanolamine-N-[methoxy(polyethylene glycol)-2000] (mPEG-DSPE).

7. The pharmaceutical composition of claim 5, wherein the combination of cationic, zwitterionic, and PEGylated anionic lipids and cholesterol is in a molar ratio of 75:5:10:10 zwitterionic lipid:PEGylated lipid:cationic lipid:Cholesterol.

8. The pharmaceutical composition of claim 1, wherein 5FURW is incorporated into the liposome at 26.6±2.4%.

9. The pharmaceutical composition of claim 1, wherein the liposome is sized 163.8±17.2 nm.

10. The pharmaceutical composition of claim 1, wherein the liposome has a zeta potential of +32.2±6.5 mV.

11. The pharmaceutical composition of claim 1, wherein the lipid composition of the liposome is 80:10:10 DSPC:DOTAP:Cholesterol.

12. The pharmaceutical composition of claim 11, wherein 5FURW is incorporated into the liposome at 26.6±2.4%.

13. The pharmaceutical composition of claim 11, wherein the liposome is sized 163.8±17.2 nm.

14. The pharmaceutical composition of claim 11, wherein the liposome has a zeta potential of +32.2±6.5 mV.

* * * * *

UNITED STATES PATENT AND TRADEMARK OFFICE
CERTIFICATE OF CORRECTION

PATENT NO. : 11,191,774 B2
APPLICATION NO. : 15/779232
DATED : December 7, 2021
INVENTOR(S) : Mitragotri et al.

Page 1 of 1

It is certified that error appears in the above-identified patent and that said Letters Patent is hereby corrected as shown below:

In the Specification

At Column 1, Lines 17-21:
"This invention was made with government support under Grant No. 1 S10 OD010610-01A1 awarded by the National Institutes of Health and Grant No. DMR 1121053 awarded by the National Science Foundation. The government has certain rights in the invention."

Should be replaced with:
— This invention was made with government support under OD010610 awarded by the National Institutes of Health and under 1121053 awarded by the National Science Foundation. The government has certain rights in the invention." —.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*